(12) United States Patent
Fu et al.

(10) Patent No.: US 12,324,798 B1
(45) Date of Patent: Jun. 10, 2025

(54) LEONURINE NANOCOMPOSITE HYDROGEL AND PREPARATION METHODS AND APPLICATIONS THEREOF

(71) Applicant: WEST CHINA HOSPITAL OF SICHUAN UNIVERSITY, Sichuan (CN)

(72) Inventors: Weili Fu, Chengdu (CN); Runze Yang, Chengdu (CN); Liwei Yan, Chengdu (CN); Jian Li, Chengdu (CN)

(73) Assignee: WEST CHINA HOSPITAL OF SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 18/977,838

(22) Filed: Dec. 11, 2024

(30) Foreign Application Priority Data

Dec. 11, 2023 (CN) .......................... 202311691342.8

(51) Int. Cl.
| | | |
|---|---|---|
| *A61K 31/235* | (2006.01) | |
| *A61K 9/06* | (2006.01) | |
| *A61K 9/51* | (2006.01) | |
| *A61K 47/42* | (2017.01) | |

(52) U.S. Cl.
CPC .............. *A61K 31/235* (2013.01); *A61K 9/06* (2013.01); *A61K 9/5146* (2013.01); *A61K 47/42* (2013.01)

(58) Field of Classification Search
CPC ...... A61K 31/235; A61K 9/06; A61K 9/5146; A61K 47/42
See application file for complete search history.

(56) References Cited

FOREIGN PATENT DOCUMENTS

| CN | 102475699 A | | 5/2012 | | |
|---|---|---|---|---|---|
| CN | 106619602 A | | 5/2017 | | |
| CN | 107737370 A | | 2/2018 | | |
| CN | 111297844 A | | 6/2020 | | |
| CN | 111423600 A | | 7/2020 | | |
| CN | 114796181 A | | 7/2022 | | |
| CN | 115645527 A | * | 1/2023 | | |
| CN | 115957348 A | * | 4/2023 | | |
| CN | 116102736 A | | 5/2023 | | |
| CN | 116196468 A | | 6/2023 | | |
| CN | 116492289 A | | 7/2023 | | |
| WO | WO-2022087750 A1 | * | 5/2022 | ............. | A23L 19/00 |
| WO | 2022226357 A | | 10/2022 | | |
| WO | WO-2022226357 A1 | * | 10/2022 | ......... | A61K 41/0057 |
| WO | 2023194414 A | | 10/2023 | | |

OTHER PUBLICATIONS

Machine translation for CN-115645527-A (Year: 2023).*
Machine translation for CN-115957348-A (Year: 2023).*
Cheng et al.; "A Multifunctional Nanoplatform against Multidrug Resistant Cancer: Merging the Best of Targeted Chemo/Gene/Photothermal Therapy"; © 2017 WILEY-VCH Verlag Gmbh & Co. KGaA, Weinheim; Adv. Funct. Mater. 2017, 27, 1704135 (15) and Supporting Information (Year: 2017).*
Xiao, Congcong et al., Research progress of anti-tumor in situ gel delivery system, Acta Pharmaceutica Sinica, 58 (10): 3004-3015, 2023.
Li, Yan et al., Research Progress of Pharmacological Action of Yimucao (Herba Leonuri), Chinese Archives of Traditional Chinese Medicine, 41(5): 102-106, 2023.
Tuğçe Şener Raman et al., A study on the material propertiess for novel PEGDA/gelatin hybrid hydrogels polymerized by electron beam irradiation, Frontiers in Chemistry, 2023, 12 Pages.
Chen, Lijuan et al., Folic Acid Adjustive Polydopamine Organic Nanoparticles Based Fluorescent Probe for the Selective Detection of Mercury Ions, Polymers, 15: 1-12, 2023.
Decision to Grant a Patent in Chinese Application No. 202311691342.8 mailed on Jan. 16, 2024, 6 pages.

* cited by examiner

*Primary Examiner* — Robert A Wax
*Assistant Examiner* — John W Lippert, III
(74) *Attorney, Agent, or Firm* — PORUS IP LLC

(57) ABSTRACT

The present disclosure relates to a field of biomedical technology. Embodiments of the present disclosure provide a leonurine nanocomposite hydrogel and preparation method and application thereof, including: dissolving dopamine (DA) monomers and inducing oxidation and self-polymerization of the DA to obtain polydopamine (PDA) nanoparticles, grafting thiol polyethylene glycol folic acid (SH-PEG-FA) on a surface of the PDA nanoparticles to obtain folic acid polydopamine (FA-PDA) nanocarriers; loading a leonurine (Leon) using the FA-PDA nanocarriers of the step 1 to obtain FA-PDA@Leon; encapsulating the FA-PDA@Leon of the step 2 into a gel matrix to obtain gel@FA-PDA@Leon hydrogel.

5 Claims, 24 Drawing Sheets gelatin+NaOH gelatin+PEGDA

PEGDA+NaOH gelatin+PEGDA+NaOH

LEONURINE NANOCOMPOSITE HYDROGEL AND PREPARATION METHODS AND APPLICATIONS THEREOF

CROSS-REFERENCE TO RELATED APPLICATIONS

This application claims priority to Chinese Patent Application No. 202311691342.8, filed on Dec. 11, 2023, the entire contents of each of which are hereby incorporated by reference.

TECHNICAL FIELD

The present disclosure relates to the field of biomedical technology, and in particular, a leonurine (Leon) nanocomposite hydrogel, preparation method and application thereof.

BACKGROUND

Rheumatoid arthritis (RA) is a chronic autoimmune inflammatory disease that primarily affects joint cartilage and bones, resulting in joint pain, swelling, stiffness and dysfunction. The cause of the RA is not clear, which is related to genetics, environment, and lifestyle. Currently, a treatment of the RA mainly relies on pharmacological interventions, including nonsteroidal anti-inflammatory drugs, glucocorticoids, disease-modifying antirheumatic drugs, and biologics, etc., while efficacies of the drugs are limited, and there are drug-resistance and side effect problems. Therefore, there is a need to find new therapeutic targets and strategies.

In recent years, more and more studies have shown that pathogenesis of the RA is related to synovial inflammation and iron death of chondrocytes. The synovial inflammation is caused by dysregulation of the body's immune function, resulting in a large number of immune cells, especially M1-type macrophages, infiltrating into synovial tissue and secreting excessive amounts of inflammatory factors and reactive oxygen species (ROS), thus causing an inflammatory response in a joint cavity. The synovial inflammation not only directly damages the joint cartilage, but also induces chondrocytes to undergo iron death through action of inflammatory mediators, i.e., ferritin lysosome/iron-dependent cell death, which is a newly discovered mode of cell death characterized by lipid peroxidation and disturbed iron metabolism. The occurrence of the iron-dependent cell death leads to apoptosis of chondrocytes and degradation of cartilage matrix, which in turn accelerates a pathological process of the RA.

Therefore, treatment targeting the synovial inflammation and the iron death is expected to achieve effective control of the RA. Traditional herbal medicines, which have a long history of application in the treatment of disease, are now receiving increasing attention due to their multiple biological benefits, and are expected to provide new therapeutic targets. As a main active ingredient extracted from motherwort, a leonurine (Leon) has good anti-inflammatory activity and can inhibit the activation of inflammation-related signaling pathways, such as nuclear factor-κB (NF-κB), mitogen-activated protein kinase (MAPK), and JAK2/STAT3 pathways, which can help to reduce the expression of pro-inflammatory cytokines and the ROS, creating a suitable environment for chondrocyte survival. However, current pharmacological interventions face challenges such as poor targeting of drugs, low bioavailability, and short duration of treatment, resulting in suboptimal drug efficacy. To overcome these problems, several new technologies and approaches have been developed for RA therapy, such as nanoparticle drug delivery systems, CRISPR-Cas9 genome editing technology, and others.

SUMMARY

In response to the above problem, the present disclosure provides a leonurine nanocomposite hydrogel, preparation method and application thereof.

The present disclosure utilizes the following technical solution:

One or more embodiments of the present disclosure provide a preparation method for a leonurine nanocomposite hydrogel, comprising:
  step 1: dissolving dopamine (DA) monomers and inducing oxidation and self-polymerization of the DA monomers to obtain polydopamine (PDA) nanoparticles, grafting thiol polyethylene glycol folic acid (SH-PEG-FA) on a surface of the PDA nanoparticles to obtain folic acid polydopamine (FA-PDA) nanocarriers;
  step 2: loading a leonurine (Leon) using the FA-PDA nanocarriers of the step 1 to obtain FA-PDA@Leon;
  step 3: encapsulating the FA-PDA@Leon of the step 2 into a gel matrix to obtain gel@FA-PDA@Leon hydrogel;
  wherein the gel@FA-PDA@Leon hydrogel is prepared by: dissolving gelatin and mixing the gelatin with the FA-PDA@Leon to obtain solution A, adding polyethylene glycol diacrylate (PEGDA) solution to the solution A and adding sodium hydroxide (NaOH) solution to adjust a pH value to obtain the gel@FA-PDA@Leon hydrogel.

In some embodiments, a mass ratio of the FA-PDA nanocarriers to the Leon in the step 2 is 20:1.

In some embodiments, in the step 1, a condition for inducing the oxidation and self-polymerization of the DA monomer is stirring and reacting for 12 hours in Tris solution at 25° C. and pH 8.5.

In some embodiments, a mass ratio of the gelatin to the FA-PDA@Leon is 640:1.

In some embodiments, the pH value ranges from 6-7.

One or more embodiments of the present disclosure provide a leonurine nanocomposite hydrogel.

One or more embodiments of the present disclosure provide an application of the leonurine nanocomposite hydrogel in the preparation of rheumatoid arthritis drugs.

BRIEF DESCRIPTION OF THE DRAWINGS

In order to more clearly illustrate the technical solutions of the embodiments of the present disclosure, the accompanying drawings of the embodiments will be briefly described below, and it will be apparent that the accompanying drawings in the following description relate only to some embodiments of the present disclosure and are not intended to be a limitation of the present disclosure.

DETAILED DESCRIPTION

Figure 1:
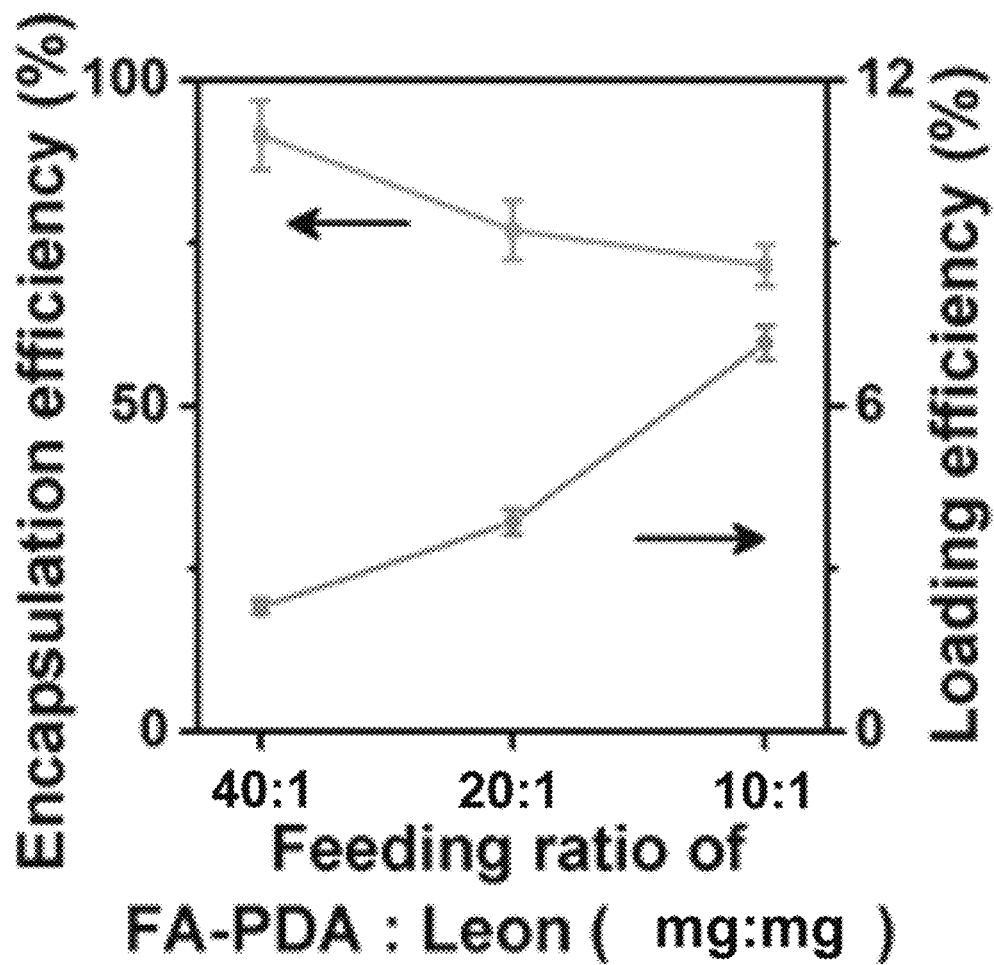
FIG. 1 is a schematic diagram illustrating an encapsulation efficiency and loading efficiency of FA-PDA nanocarriers for leonurine according to some embodiments of the present disclosure.

In order to make the purpose, technical solutions and advantages of the embodiments of the present disclosure clearer, the technical solutions of the embodiments of the present disclosure will be described clearly and completely below in conjunction with the accompanying drawings of the embodiments of the present disclosure. Obviously, the described embodiments are a part of the embodiments of the present disclosure, and not all of the embodiments. Based on the described embodiments of the present disclosure, all other embodiments obtained by a person of ordinary skill in the art without the need for creative labor fall within the scope of protection of the present disclosure.

The present disclosure is further described below in connection with the accompanying drawings and embodiments.

Embodiments of the present disclosure provide an injectable bioadhesive hydrogel for treatment of rheumatoid arthritis (RA). The hydrogel may form in joint cavity and adhere closely to cartilage tissues, thereby releasing folate-modified dopamine nanomaterials containing the anti-inflammatory drug Leon, inhibiting synovial inflammation and iron-dependent cell death, protecting the cartilage tissues and restoring joint function.

The present disclosure provides a preparation method for a leonurine nanocomposite hydrogel, comprising:

step 1: dissolving dopamine (DA) monomers and inducing oxidation and self-polymerization of the DA monomers to obtain polydopamine (PDA) nanoparticles, grafting thiol polyethylene glycol folic acid (SH-PEG-FA) on a surface of the PDA nanoparticles to obtain folic acid polydopamine (FA-PDA) nanocarriers.

The dopamine (DA) monomer is a monoamine neurotransmitter, belonging to catecholamine and phenethylamine families of an organic compound. The DA plays key roles in a central nervous system, a hormonal system, and kidneys.

The polydopamine (PDA) nanoparticles are biopolymers produced by oxidative polymerization of the DA monomers.

The thiol-polyethylene glycol-folic acid (SH-PEG-FA) is a labeling reagent that combines a variety of chemical and biologically active components. The SH-PEG-FA is composed of chondroitin sulfate (or a similar group), polyethylene glycol (PEG), and folic acid. In some embodiments, an average molecular weight of polyethylene glycol (PEG) segments is about 5000 Dalton (Da), or the like.

In some embodiments, grafting the SH-PEG-FA on a surface of the PDA nanoparticles is achieved by chemically bonding a sulfhydryl group of the SH-PEG-FA to the surface of the PDA or other reactive groups, thereby achieving immobilization of the SH-PEG-FA on the PDA nanoparticles, thereby obtaining the FA-PDA nanocarriers.

In some embodiments, conditions for the oxidation and self-polymerization of the DA monomer may include multiple. For example, the conditions for the oxidation and self-polymerization of the DA monomer may include a temperature of the oxidation and self-polymerization, a pH value of added Tris solution, and a stirring reaction time.

In some embodiments, a condition for inducing the oxidation and self-polymerization of the DA monomer is stirring and reacting for 12 hours in Tris solution at 25° C. and pH 8.5.

In some embodiments, a condition for inducing the oxidation and self-polymerization of the DA monomer is stirring and reacting for 13 hours in Tris solution at 26° C. and pH 8.7.

In some embodiments, a condition for inducing the oxidation and self-polymerization of the DA monomer is stirring and reacting for 11 hours in Tris solution at 24° C. and pH 8.3.

In some embodiments, the condition for the oxidation and self-polymerization of the DA monomer (the temperature, the pH value of the Tris solution, and the stirring reaction time, etc.) may be preset according to practical needs.

Step 2: loading a leonurine (Leon) using the FA-PDA nanocarriers of the step 1 to obtain FA-PDA@Leon;

The FA-PDA@Leon is PDA nanoparticles loaded with Leon surface-grafted with the SH-PEG-FA.

The leonurine (Leon) is an alkaloid extracted from plant Motherwort, family Labiatae, with antioxidant, anti-inflammatory, anti-tumor, and cardiovascular protective effects.

In some embodiments, the loading the leonurine (Leon) using the FA-PDA nanocarriers refers to immobilizing or encapsulating the Leon on the FA-PDA nanocarriers by a particular manner.

In some embodiments, a mass ratio of the FA-PDA nanocarriers to the Leon in the step 2 is one of 22:1, 20:1, or 18:1. In some embodiments, the mass ratio of the FA-PDA nanocarriers to the Leon is set according to actual needs.

In some embodiments, the mass ratio of the FA-PDA nanocarriers to the Leon is determined based on a combination of experimental results, more descriptions may be found in FIG. 1 below.

Step 3: encapsulating the FA-PDA@Leon of the step 2 into a gel matrix to obtain gel@FA-PDA@Leon hydrogel. Encapsulation is wrapping one substance (usually an active substance or drug) in another substance to protect the substance from external environment and enhance its physicochemical properties or control its rate of release.

The gel matrix is a material used to form the gel, typically including a polymer material, such as gelatin, water, cellulose derivatives, or glycerol.

The gel@FA-PDA@Leon hydrogel is hydrogel formed by encapsulating the PDA nanoparticles loaded with the Leon surface-grafted with the SH-PEG-FA into the gel matrix. The gel@FA-PDA@Leon hydrogel may also be referred to as the hydrogel.

In some embodiments, a preparation method for the gel@FA-PDA@Leon hydrogel includes: dissolving and mixing the gelatin with the FA-PDA@Leon to obtain solution A, adding polyethylene glycol diacrylate (PEGDA) solution to the solution A and adding sodium hydroxide (NaOH) solution to adjust a pH value to obtain the gel@FA-PDA@Leon hydrogel.

The solution A is a mixture of the gelatin and the FA-PDA@Leon.

In some embodiments, a mass ratio of the gelatin to the FA-PDA@Leon is one of 630:1, 635:1, 640:1, 645:1, or 650:1. In some embodiments, the mass ratio of the gelatin to the FA-PDA@Leon is set according to the actual needs.

In some embodiments, the pH value is adjusted by adding the NaOH solution, and the solution for preparing the gel@FA-PDA@Leon hydrogel is required to be adjusted to a pH value within a preset range.

In some embodiments, the pH value ranges from 6-7.

In some embodiments, the pH value ranges from 6.5-7.

In some embodiments, the preset range of the pH value to be adjusted for the preparation of the gel @FA-PDA@Leon hydrogel solution is set according to the actual requirements.

In some embodiments of the present disclosure, there are highly reactive catechol groups on the surface of the PDA nanocarriers, which facilitates surface modification of the folate ligand by Michael addition reaction. The catechol moieties on the nanocarriers may interact non-covalently with the hydrophobic Leon via π-π stacking, which enables effective immobilization of the drug on the nanocarriers. The antioxidant catechol group can protect the Leon from ROS damage and maintain its activation in the inflammatory environment. Therefore, the PDA nanocarriers containing abundant catechol moieties are ideal candidates for Leon delivery.

According to some embodiments of the present disclosure, the leonurine nanocomposite hydrogel is obtained by using the preparation method for the leonurine nanocomposite hydrogel.

In some embodiments of the present disclosure, the leonurine nanocomposite hydrogel has good injectability, bioadhesion, and anti-inflammatory properties, and is capable of being injected into the joint cavity to form a gel and tightly attach to the cartilage tissues, so as to prolong the residence time of the nanomedicine in the joint cavity and improve the treatment effect.

In some embodiments of the present disclosure, the leonurine nanocomposite hydrogel is capable of inhibiting synovial inflammation by down-regulating the Janus kinase/signal transducer and activator of transcription (JAK2/STAT3) signaling pathway. Meanwhile, the leonurine nanocomposite hydrogel can also protect the articular cartilage by inhibiting the iron death of chondrocytes, thus realizing the effective treatment of rheumatoid arthritis. The JAK2/STAT3 signaling pathway transmits signals from a variety of cytokines and growth factors within cells, and is widely involved in biological processes such as cell proliferation, differentiation, survival, migration, and apoptosis.

In some embodiments of the present disclosure, the leonurine nanocomposite hydrogelis capable of acting as a localized reservoir of the nanomedicine, preventing its rapid diffusion and clearance within the joint cavity, and thereby improving the bioavailability and therapeutic efficiency of the drug. The leonurine nanocomposite hydrogel is able to gradually degrade in response to the stimulation of the joint fluid, thereby releasing the nanomedicine. The leonurine nanocomposite hydrogel is able to synergize with the nanomedicine to exert anti-inflammatory and antioxidant effects, which can inhibit inflammatory responses of M1-type macrophages, protect chondrocytes from damage due to iron death, and maintain the structural integrity of articular cartilage and accelerate the recovery of joint function.

The following embodiments are some more specific illustrations of embodiments related to some of the above embodiments. Some of these embodiments can also be replaced or combined with corresponding elements in other embodiments to form new embodiments. The experimental methods in the following embodiments are conventional if not otherwise stated. The experimental materials used in the following embodiments are, if not otherwise specified, obtained by purchase from a conventional biochemical reagent company. The quantitative tests in the following embodiments were set up with three repetitions of the experiment, and the results were averaged. It should be appreciated that the following embodiments are intended to better explain the present disclosure and are not intended to limit the present disclosure.

Embodiments

Embodiment 1 Determination of a Mass Ratio of FA-PDA Nanocarriers to Leon

FIG. 1 is a schematic diagram illustrating an encapsulation efficiency and loading efficiency of FA-PDA nanocarriers for leonurine according to some embodiments of the present disclosure.

In some embodiments, a mass ratio of each component of the leonurine nanocomposite hydrogel is optimized based on data on gelation state and gelation time of the leonurine nanocomposite hydrogel during preparation. For example, the mass ratio of the FA-PDA nanocarriers to the Leon is determined by balancing the encapsulation efficiency and loading efficiency of the leonurine nanocomposite hydrogel in the preparation process.

The gelation state is a process by which the hydrogel is transformed from a liquid state to a gel state under a specific condition.

The gelation time is a time it takes for the hydrogel to change from the liquid state to the gel state.

The encapsulation efficiency is a ratio of encapsulated Leon to total input Leon in the hydrogel. The encapsulation efficiency reflects an efficiency of the encapsulation of Leon in the hydrogel, i.e., how much Leon are successfully encapsulated by the hydrogel.

The loading efficiency is a ratio of an actual Leon contained in the hydrogel to the total mass of a drug-carrying hydrogel, which indicates an amount of the Leon that the hydrogel can carry.

In some embodiments, 100 mg of the FA-PDA nanoparticles were suspended and dispersed in 100 mL of deionized water, and 10 mL of Leon solution at different concentrations (e.g., 0.25 mg/mL, 0.5 mg/mL, and 1 mg/mL) were added respectively, which in turn yielded the FA-PDA nanocarrier to the Leon at mass ratios of 40:1, 20:1, and 10:1, respectively. After 12 h of reaction at 25° C., the reaction was centrifuged at 10,000 rpm, spinning for 5 min, and thus the supernatant was collected. A concentration of free Leon in the supernatant was determined using a nanodrop analyzer for different mass ratios, respectively.

As shown in FIG. 1, the encapsulation efficiency of the FA-PDA nanocarriers for the Leon decreases with the increase of the mass ratio of the FA-PDA nanocarriers to the Leon, while the loading efficiency increases with the increase of the mass ratio of the FA-PDA nanocarriers to the Leon. Thus, taking into account the trade-off between encapsulation efficiency and loading efficiency, the mass ratio of the FA-PDA nanocarriers to the Leon was selected to be 20:1 as well as a mass ratio close to 20:1.

Embodiment 2 Determination Whether a Mix of Different Components Forms a Gel

FIG. 2A-FIG. 2D are schematic diagrams illustrating at least two mixed solutions in gelatin, Polyethylene Glycol Diacrylate (PEGDA), and sodium hydroxide (NaOH) respectively according to some embodiments of the present disclosure.

Figure 2A:
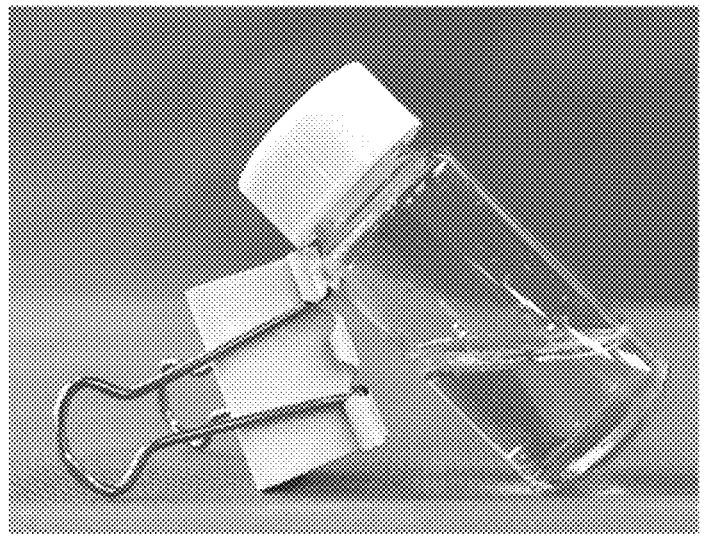
FIG. 2A-FIG. 2D are schematic diagrams illustrating at least two mixed solutions in gelatin, Polyethylene Glycol Diacrylate (PEGDA), and sodium hydroxide (NaOH) respectively according to some embodiments of the present disclosure.
Figure 2B:
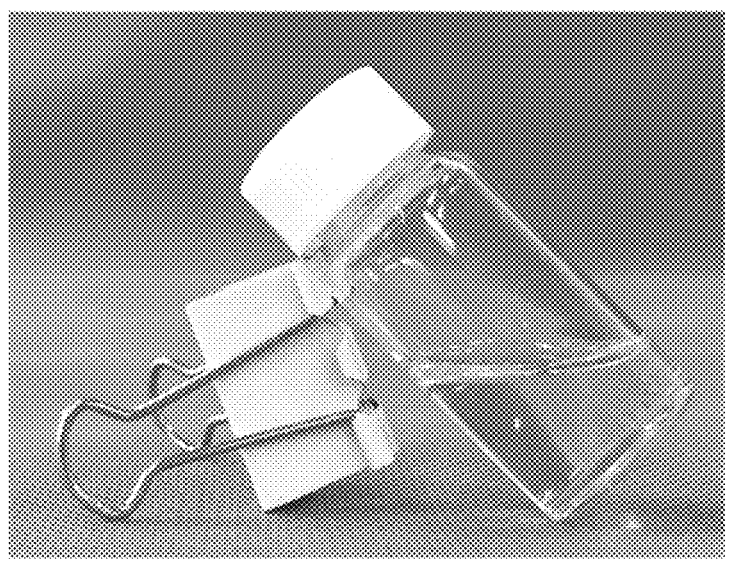
Figure 2C:
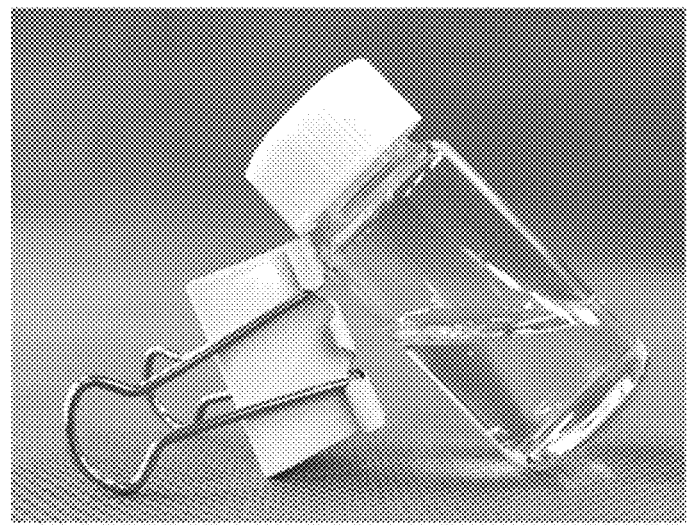
Figure 2D:
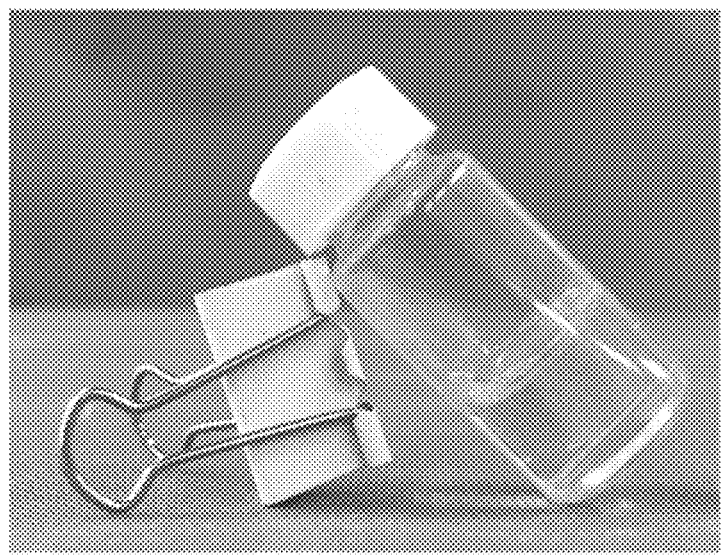

As shown in FIG. 2A, FIG. 2B, and FIG. 2C, solution in bottle is liquid with good fluidity. As shown in FIG. 2D, the solution in the bottle is less fluid and is a gel. It can be seen that the gelatin mixed with the NaOH solution in FIG. 2A cannot form the gel. In FIG. 2B, mixing the gelatin with the PEGDA cannot form the gel. In FIG. 2C, mixing the PEGDA with the NaOH cannot form the gel. Mixing the gelatin with the PEGDA and the NaOH is required to form the gel.

Embodiment 3 Determination Mass of the Gelatin, the PEGDA, and the NaOH

Figure 3A:
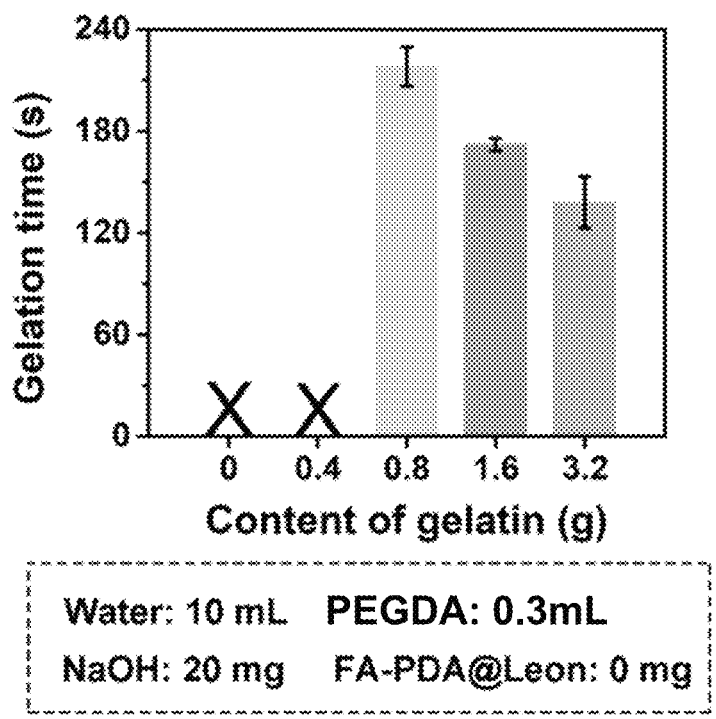
FIG. 3A is a schematic diagram illustrating gelation time of hydrogels with different gelatin concentrations according to some embodiments of the present disclosure.
Figure 3B:
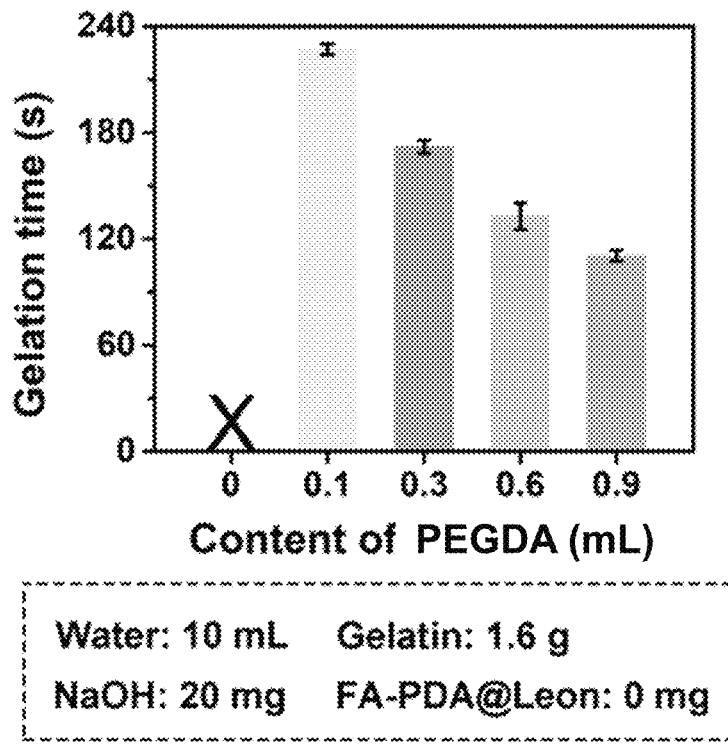
FIG. 3B is a schematic diagram illustrating gelation time of hydrogels corresponding to different PEGDA concentrations according to some embodiments of the present disclosure.
Figure 3C:
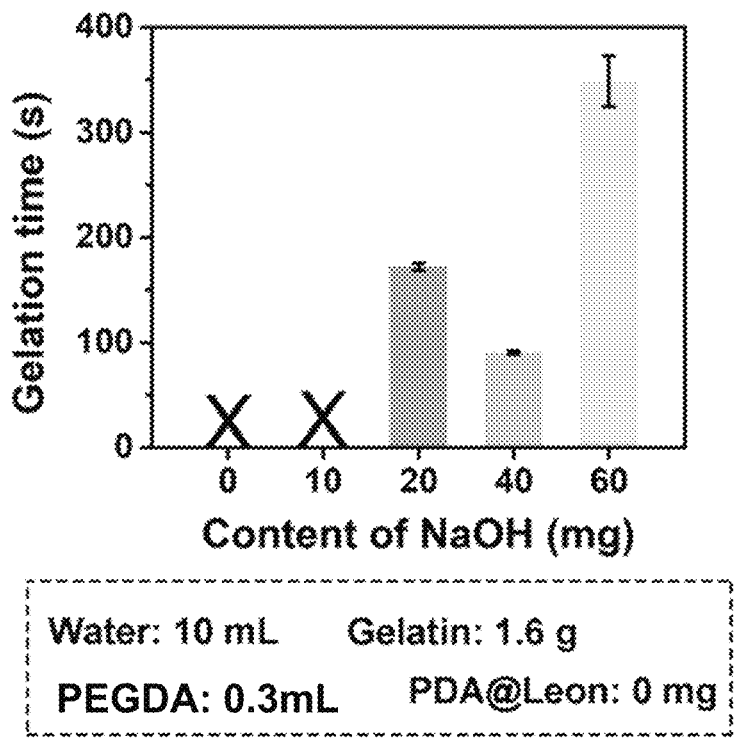
FIG. 3C is a schematic diagram illustrating gelation time of hydrogels corresponding to different NaOH concentrations according to some embodiments of the present disclosure.
Figure 3D:
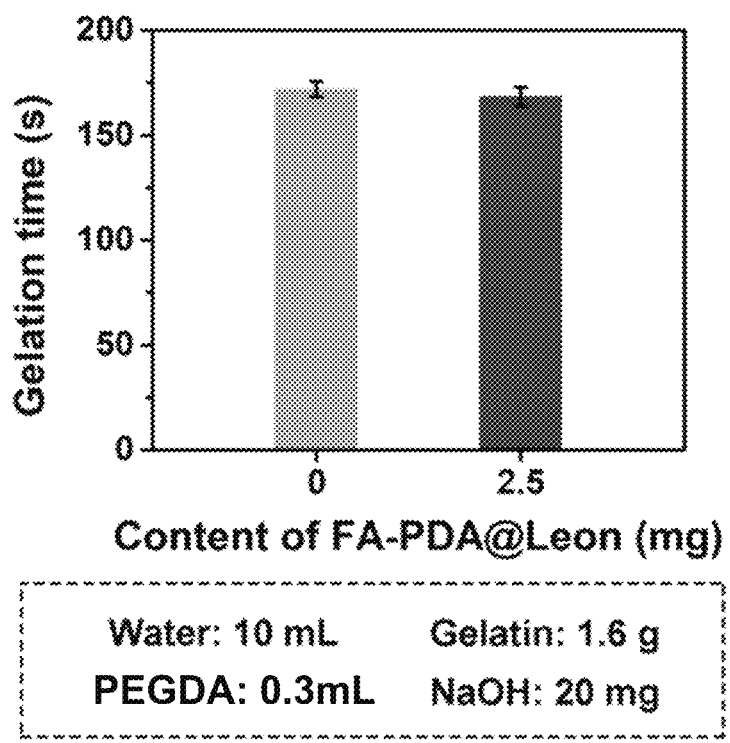
FIG. 3D is a schematic diagram illustrating gelation time of hydrogels corresponding to whether FA-PDA@Leon is encapsulated according to some embodiments in the present disclosure.

FIG. 3A is a schematic diagram illustrating gelation time of hydrogels with different gelatin concentrations according to some embodiments of the present disclosure. FIG. 3B is a schematic diagram illustrating gelation time of hydrogels corresponding to different PEGDA concentrations according to some embodiments of the present disclosure. FIG. 3C is a schematic diagram illustrating gelation time of hydrogels corresponding to different NaOH concentrations according to some embodiments of the present disclosure. FIG. 3D is a schematic diagram illustrating gelation time of hydrogels corresponding to whether FA-PDA@Leon is encapsulated according to some embodiments in the present disclosure.

Because the hydrogel needs to be injected into a joint cavity of an animal, if the gel time of the hydrogel is too short, the hydrogel may be formed into a gel in a syringe, which is not conducive to performing the injection operation; and if the gel time of the hydrogel is too long, the hydrogel is prone to spreading inside the joint cavity after the injection, which in turn unable to act at the designated location in the joint cavity. The gelation time of the hydrogel needs to be suitable, such as a suitable gel time of the hydrogel is 2-3 minutes or the like. The gelation time of the hydrogel is a time required to change from the liquid state to the solid state.

In some embodiments, the gelation times of the hydrogels corresponding to different contents of the gelatin, the PEGDA, and the NaOH may be sequentially determined using the inverted tube manner, respectively.

As shown in FIG. 3A, under a same condition, different contents of the gelatin correspond to the hydrogels with different gelation times. For example, gelation is not possible at a gelatin content of 0.4 g, a gelation time is about 220 seconds at a gelatin content of 0.8 g, a gelation time is about 170 seconds at a gelatin content of 1.6 g, a gelation time is about 140 seconds at a gelatin content of 3.2 g.

As shown in FIG. 3B, under a same condition, different contents of the PEGDA corresponded to the hydrogels with different gelation times. For example, a gelation time is about 220 seconds at a PEGDA content of 0.1 mL; a gelation time is about 170 seconds at a PEGDA content of 0.3 mL; a gelation time is about 130 seconds at a PEGDA content of 0.6 mL; a gelation time is about 110 seconds at a PEGDA content of 0.9 mL; more content of the PEGDA, the shorter of the gelation time.

As shown in FIG. 3C, under a same condition, different contents of the NaOH corresponded to the hydrogels with different gelation times. For example, gelation is not possible at a NAOH content of 10 mg; a gelation time is about 170 seconds at a NAOH content of 20 mg; a gelation time is about 100 seconds at a NAOH content of 40 mg; a gelation time is about 350 seconds at a NAOH content is 60 mg.

In some embodiments, as shown in FIG. 3D, there is little difference in the hydrogel gelation time for hydrogels corresponding to whether or not FA-PDA@Leon is encapsulated. A suitable hydrogel has a gelation time of 2-3 min, and by combining the gelation times shown in FIG. 3A through FIG. 3D, it may be determined that the corresponding gelatin has a mass of 1.6 g, a mass of the PEGDA is 0.3 mL, and 20 mg of the NaOH. A mass of the FA-PDA@Leon encapsulated by the hydrogel is 2.5 mg.

Embodiment 4 Preparation of Gel@FA-PDA@Leon Hydrogel

Step 1: DA was induced to undergo oxidation and self-polymerization by dissolving 100 mg of the DA in 200 mL of Tris buffer (10 mm; pH=8.5) with stirring at 25° C. After 12 h of reaction, a supernatant was centrifuged three times at centrifugation conditions of 10,000 rpm for 5 min to obtain the FA-PDA nanocarriers.

Step 2: 100 mg of the FA-PDA nanocarrier was suspended in 100 ml of deionized water. Then 5 mg of the Leon was dissolved in 10 mL of Dimethyl sulfoxide (DMSO) and added to the above suspension. After reacting at 25° C. for 12 h, the FA-PDA@Leon was obtained by centrifugation 3 times at centrifugation conditions 10000 rpm, 5 min.

Step 3: First a phase separation gel-based hydrogel (Gel) was prepared: a gel hydrogel was prepared by mixing the PEGDA with the gelatin to induce phase separation. 1.6 g of the gelatin was dissolved in 10 mL of the deionized water at 37° C. and then mixed with 300 µL of the PEGDA. The pH value was adjusted with 20 mg NaOH in the pH value range of 6-7 to form a gelatin hydrogel.

In some embodiments, the gel/FA-PDA@Leon hydrogel was prepared by encapsulating the FA-PDA@Leon into a gel matrix. 1.6 g of the gelatin was dissolved in 10 mL of the deionized water and mixed with 2.5 mg of the FA-PDA@Leon at 37° C. to obtain solution A; 300 µL of PEGDA and 20 mg NaOH were added to the solution A to form the gel/FA-PDA@Leon hydrogel.

Figure 4A:
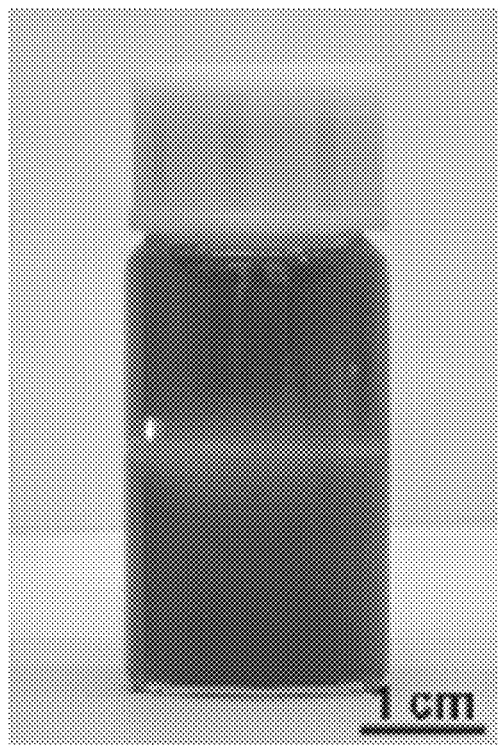
FIG. 4A is a schematic diagram illustrating a Tyndall effect of hydrogel according to some embodiments of the present disclosure.
Figure 4B:
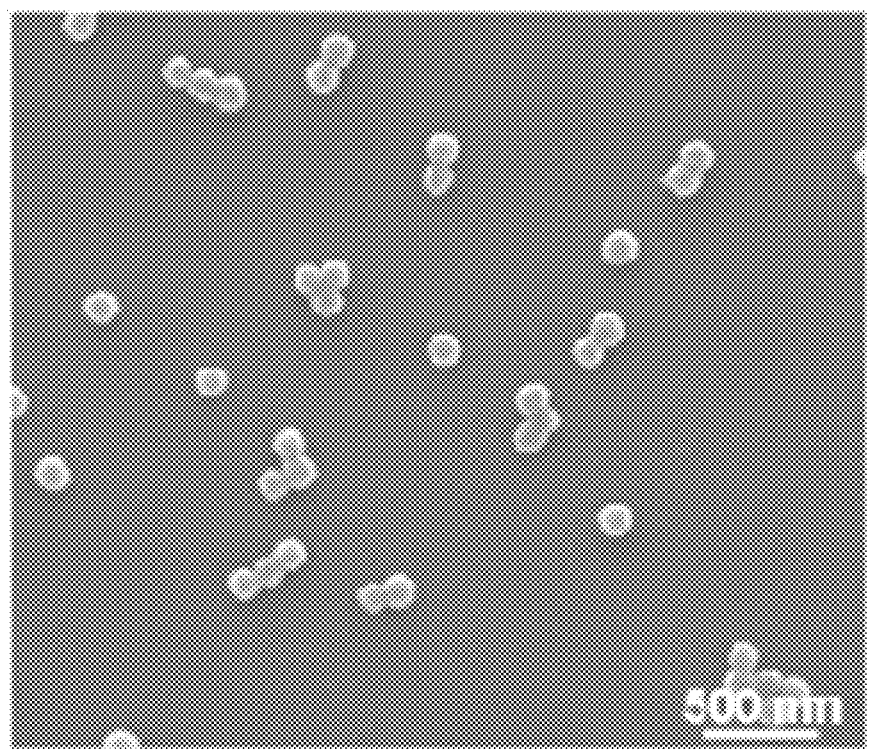
FIG. 4B is a schematic diagram illustrating a nano scanning electron microscope image of FA-PDA@Leon according to some embodiments of the present disclosure.
Figure 4C:
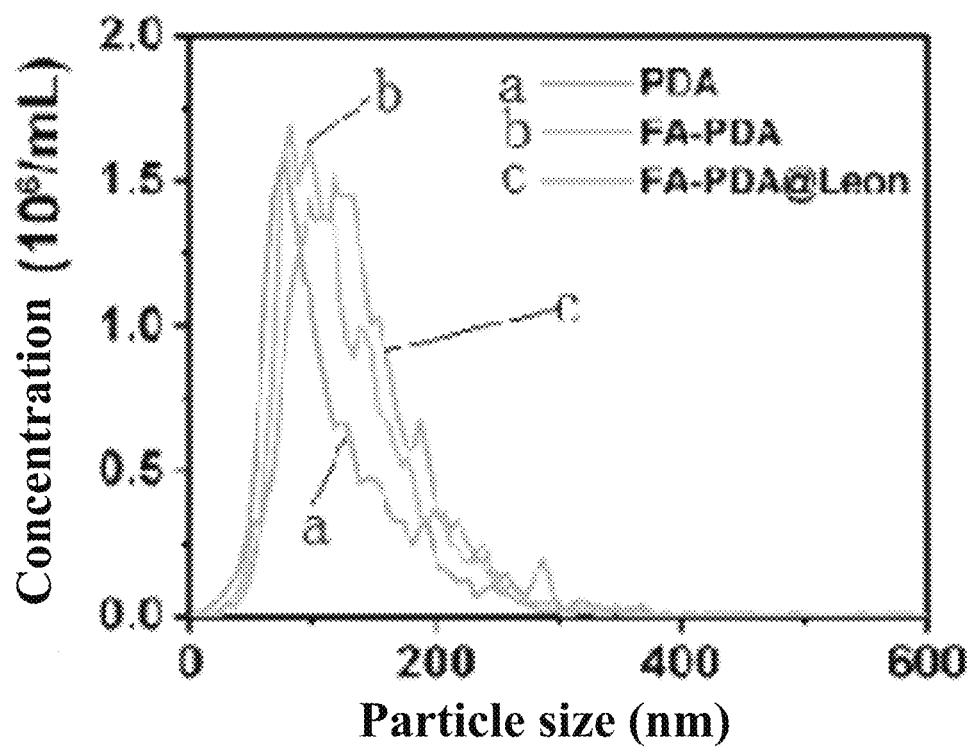
FIG. 4C is a schematic diagram illustrating nanoparticle tracking analysis (NTA) according to some embodiments of the present disclosure.
Figure 4D:
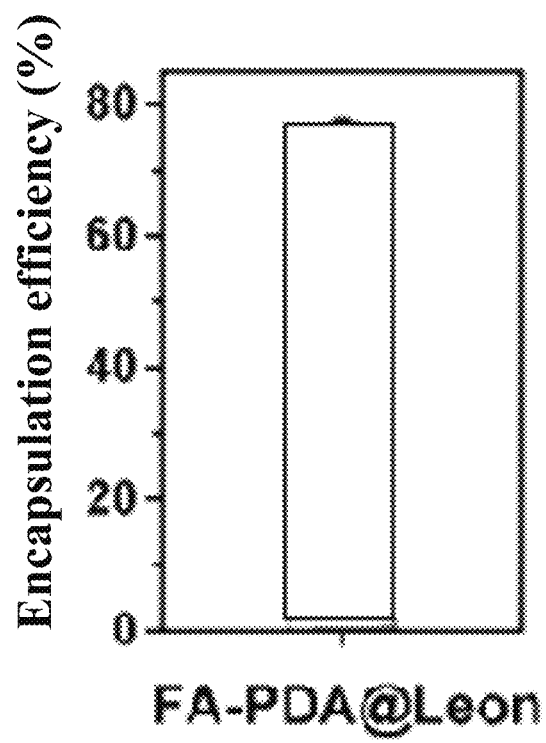
FIG. 4D is a schematic diagram illustrating an encapsulation efficiency of FA-PDA@Leon according to some embodiments of the present disclosure.
Figure 4E:
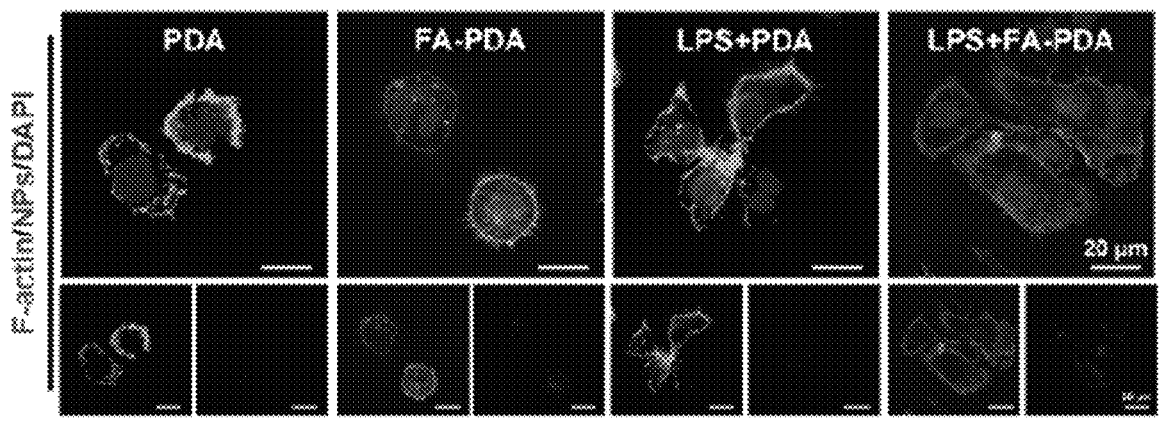
FIG. 4E is a schematic diagram illustrating rhodamine fluorescence of Raw264.7 cells incubated with FA-PDA nanoparticles according to some embodiments of the present disclosure.
Figure 4F:
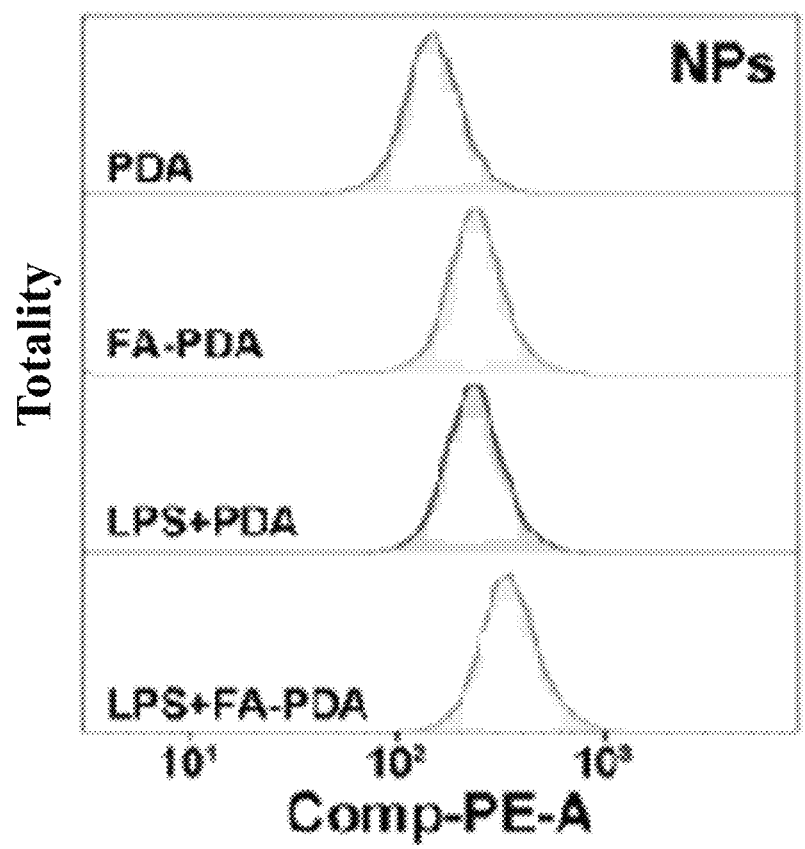
FIG. 4F is a schematic diagram illustrating a hydrogel flow cytometry plot according to some embodiments of the present disclosure.
Figure 4G:
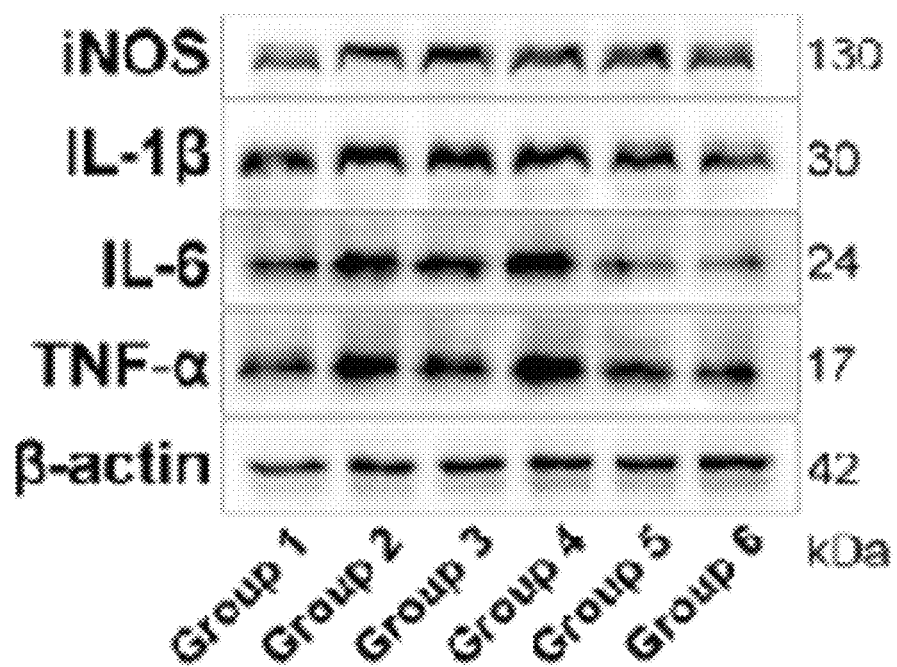
FIG. 4G is a schematic diagram illustrating hydrogel western blotting (WB) analysis image according to some embodiments of the present disclosure.
Figure 4H:
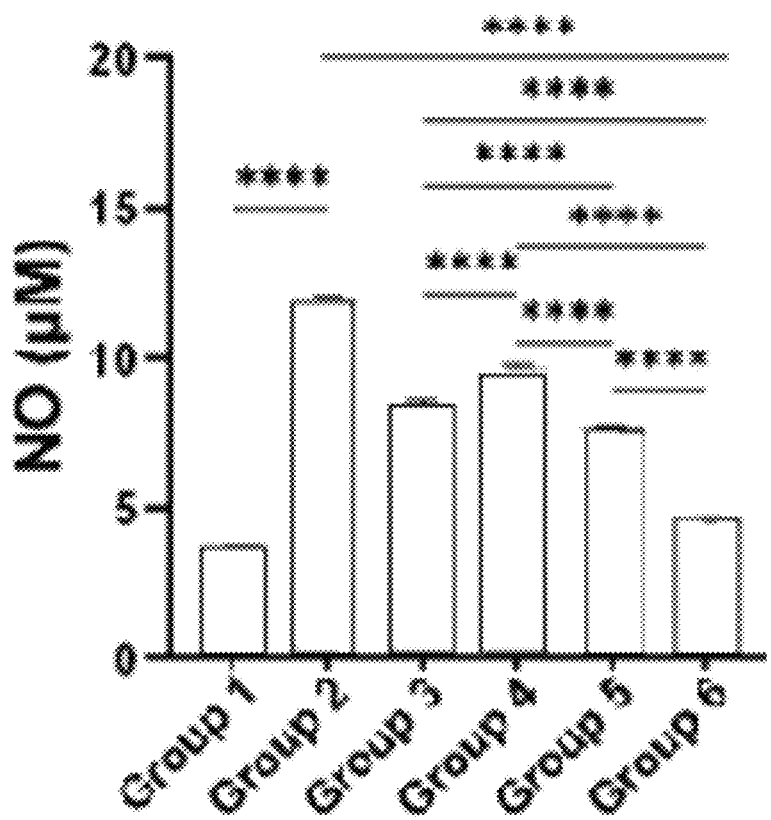
FIG. 4H is a schematic diagram illustrating FA-PDA@Leon inhibition the release of inflammatory mediator nitric oxide (NO) secreted by macrophages according to some embodiments of the present disclosure.
Figure 4I:
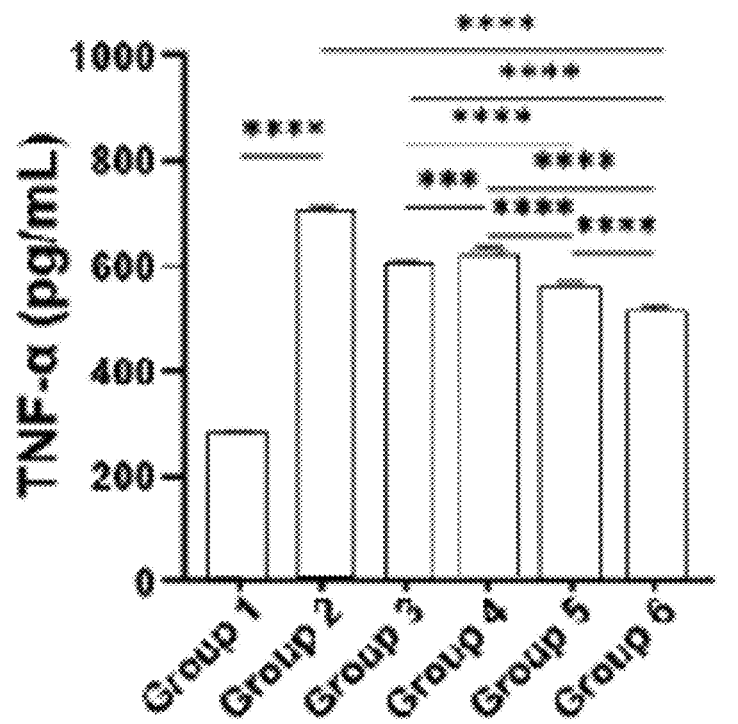
FIG. 4I is a schematic diagram illustrating an inhibitory effect of FA-PDA@Leon on expression of pro-inflammatory cytokine proteins in macrophages according to some embodiments of the present disclosure.
Figure 4I:
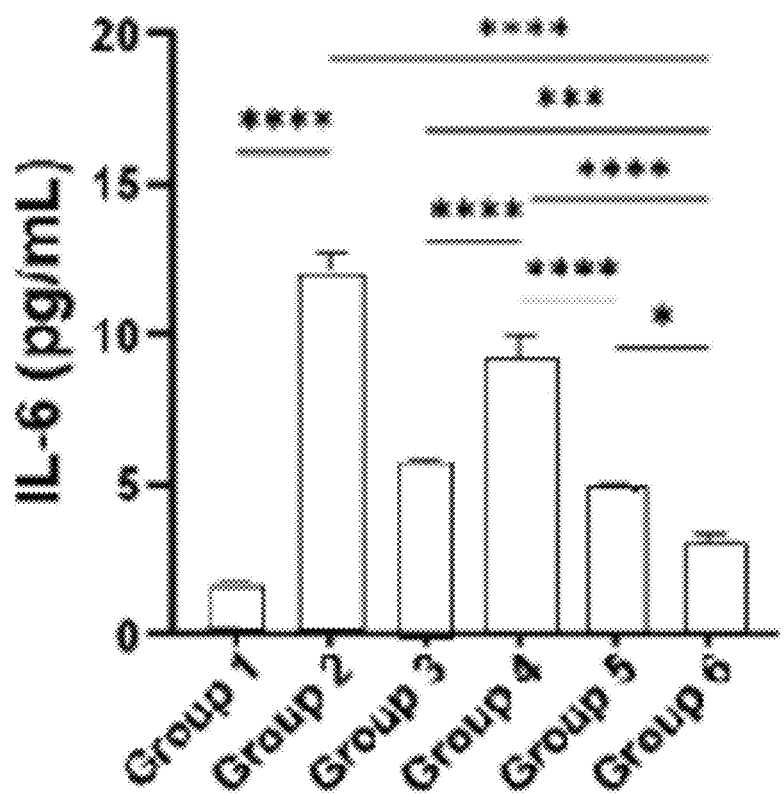
Figure 4J:
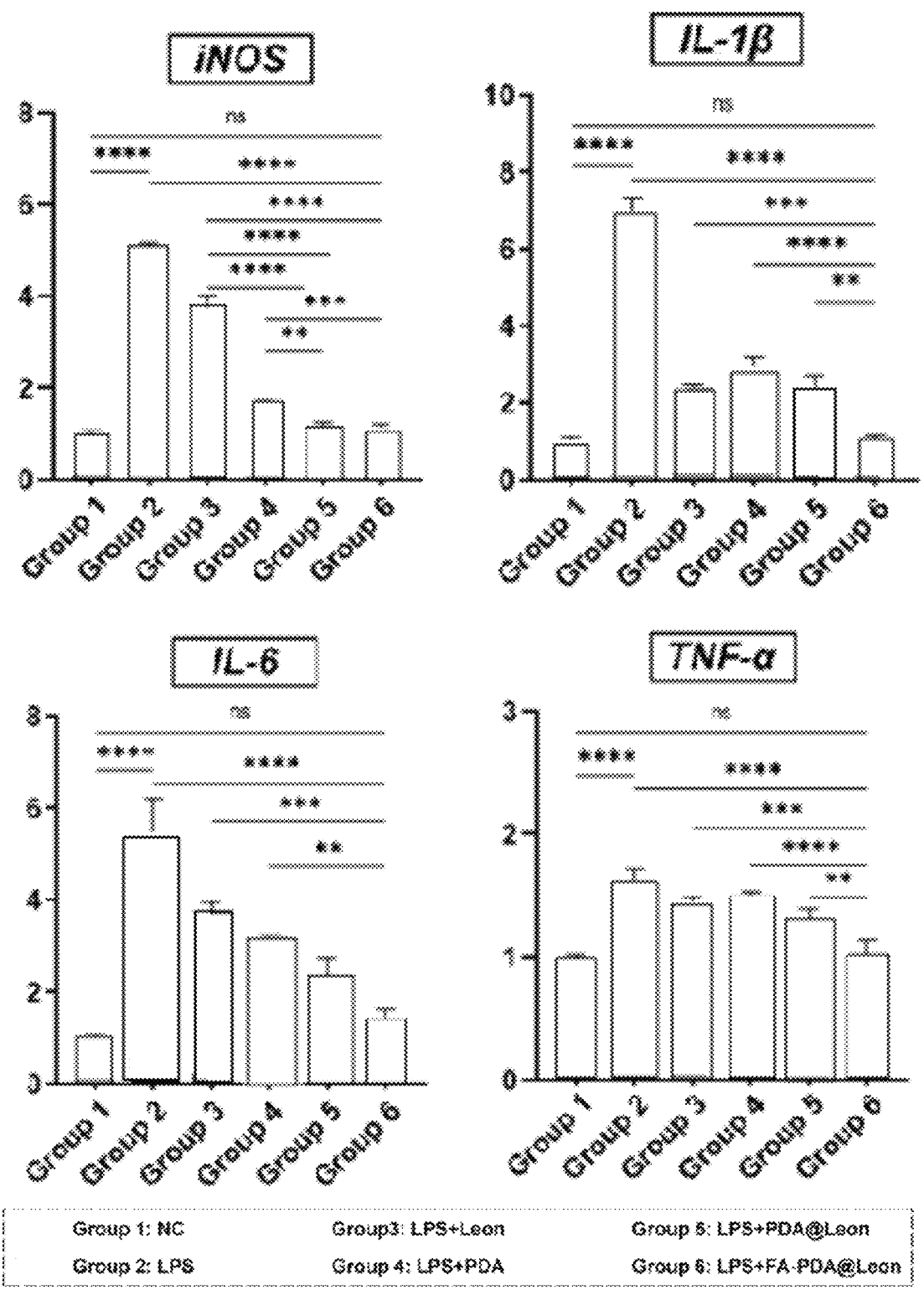
FIG. 4J is a schematic diagram illustrating real-time quantitative polymerase chain reaction (qRT-PCR) analysis according to some embodiments of the present disclosure.

FIG. 4A-FIG. 4J are schematic diagram illustrating evaluating performance of hydrogel. FIG. 4A is a schematic diagram illustrating a Tyndall effect of hydrogel according to some embodiments of the present disclosure. FIG. 4B is a schematic diagram illustrating a nano scanning electron microscope image of FA-PDA@Leon according to some embodiments of the present disclosure. FIG. 4C is a schematic diagram illustrating nanoparticle tracking analysis (NTA) according to some embodiments of the present disclosure. FIG. 4D is a schematic diagram illustrating an encapsulation efficiency of FA-PDA@Leon according to some embodiments of the present disclosure. FIG. 4E is a schematic diagram illustrating rhodamine fluorescence of Raw264.7 cells incubated with FA-PDA nanoparticles according to some embodiments of the present disclosure. FIG. 4F is a schematic diagram illustrating a hydrogel flow cytometry plot according to some embodiments of the present disclosure. FIG. 4G is a schematic diagram illustrating hydrogel western blotting (WB) analysis image according to some embodiments of the present disclosure. FIG. 4H is a schematic diagram illustrating FA-PDA@Leon inhibition the release of inflammatory mediator nitric oxide (NO) secreted by macrophages according to some embodiments of the present disclosure. FIG. 4I is a schematic diagram illustrating an inhibitory effect of FA-PDA@Leon on expression of pro-inflammatory cytokine proteins in macrophages according to some embodiments of the present disclosure. FIG. 4J is a schematic diagram illustrating real-time quantitative polymerase chain reaction (qRT-PCR) analysis according to some embodiments of the present disclosure.

The formed FA-PDA@Leon nanomedicine is well dispersed in the deionized water as can be seen by the Tyndall effect as shown in FIG. 4A. The scanning electron microscopy image as shown in FIG. 4B shows that the FA-PDA@Leon nanodrugs are spherical in shape and have a uniform diameter of about 100 nm, which is similar to that of the PDA and FA-PDA nanoparticles, and this nanosize facilitates internalization into cells.

The nanoparticle tracking analysis (NTA) as shown in FIG. 4C indicated that the hydrodynamic diameters of PDA nanoparticles are slightly enlarged in an order of FA-PDA and FA-PDA@Leon, corresponding to the surface modification and drug-loading processes during the preparation of the FA-PDA@Leon. As shown in FIG. 4D, the Leon encapsulation efficiency of the FA-PDA nanocarriers is 77.5% as calculated by Leon calibration curve. From the above results, it can be seen that FA-modified and Leon loaded FA-PDA@Leon nanodrugs have been successfully prepared.

Activated M1 macrophages are one of the main causative cells causing inflammation in RA joints. The FA-PDA@Leon nanomedicine may target into the M1 macrophages and deliver anti-inflammatory Leon inside the cells, which is favorable for improving the therapeutic efficiency of the Leon. To evaluate the targeting and cellular uptake ability of the FA-PDA nanocarriers on the M1 macrophages, macrophages represented by the Raw264.7 cells were incubated with rhodamine-labeled nanoparticles in both resting and activated states, and then observed under a fluorescence microscope. Lipopolysaccharide (LPS) is used to induce activation of the Raw264.7 toward a pro-inflammatory M1-polarized phenotype.

As shown in FIG. 4E, the rhodamine fluorescence signals of FA-PDA nanoparticles incubated with Raw264.7 cells were significantly stronger than those of the PDA group, which suggests that the surface modification of folic acid promotes, through folic acid-mediated ligand-receptor specific recognition, the enrichment and uptake of FA-PDA nanoparticles by macrophages. In addition, the FA-PDA nanoparticles cultured with LPS stimulated the strongest rhodamine fluorescence signal in the Raw264.7 cells. This is due to the fact that more folate receptors were expressed and exposed on the surface of Raw264.7 cells after LPS stimulation, which provided more binding sites to attract FA-PDA nanoparticles to be internalized into M1 macrophages.

As shown in FIG. 4F, the flow cytometric analysis further demonstrated that the FA-PDA nanocarriers have higher targeting and cellular uptake capacity for the M1 macrophages.

In some embodiments, to assess whether M1 macrophage-targeted FA-PDA nanocarriers enhance the efficiency of anti-inflammatory therapy with loaded Leon, FA-PDA@Leon was co-cultured with LPS-stimulated Raw264.7 cells for 2 days, after which western blotting (WB) analysis was performed. A first group (Group 1) in FIG. 4G to FIG. 4J represents the control group (NC), a second group (Group 2) represents the LPS treatment, a third group (Group 3) represents the LPS and Leon co-treatment, a fourth group (Group 4) represents the LPS and PDA co-treatment, the fifth group (Group 5) represents the LPS and PDA@Leon co-treatment, and a sixth group (Group 6) indicates the LPS and FA-PDA@Leon co-treatment.

As shown in FIG. 4G, LPS stimulation significantly promoted the protein expression of pro-inflammatory cytokines, including inducible nitric oxide synthase (iNOS), interleukin (IL)-13, IL-6, and tumor necrosis factor (TNF)-α. In contrast, the expression of these cytokines was down-regulated after co-culture with Leon or PDA, PDA@Leon, or FA-PDA@Leon. In particular, FA-PDA@Leon-treated cells had the lowest levels of cytokine protein expression in these treatment groups.

As shown in FIG. 4H, FA-PDA@Leon also inhibited the release of nitric oxide (NO), an inflammatory mediator secreted by macrophages. As shown in FIG. 4I, enzyme-linked immunosorbent assay (ELISA) and immunofluorescence double staining further showed that FA-PDA@Leon had a stronger inhibitory effect on macrophage pro-inflammatory cytokine protein expression compared to the other treatment groups. As shown in FIG. 4J, real-time quantitative polymerase chain reaction (qRT-PCR) analysis confirmed the trend at the genetic level.

Embodiment 5 Testing Anti-Inflammatory Activity of the Hydrogel

Figure 5A:
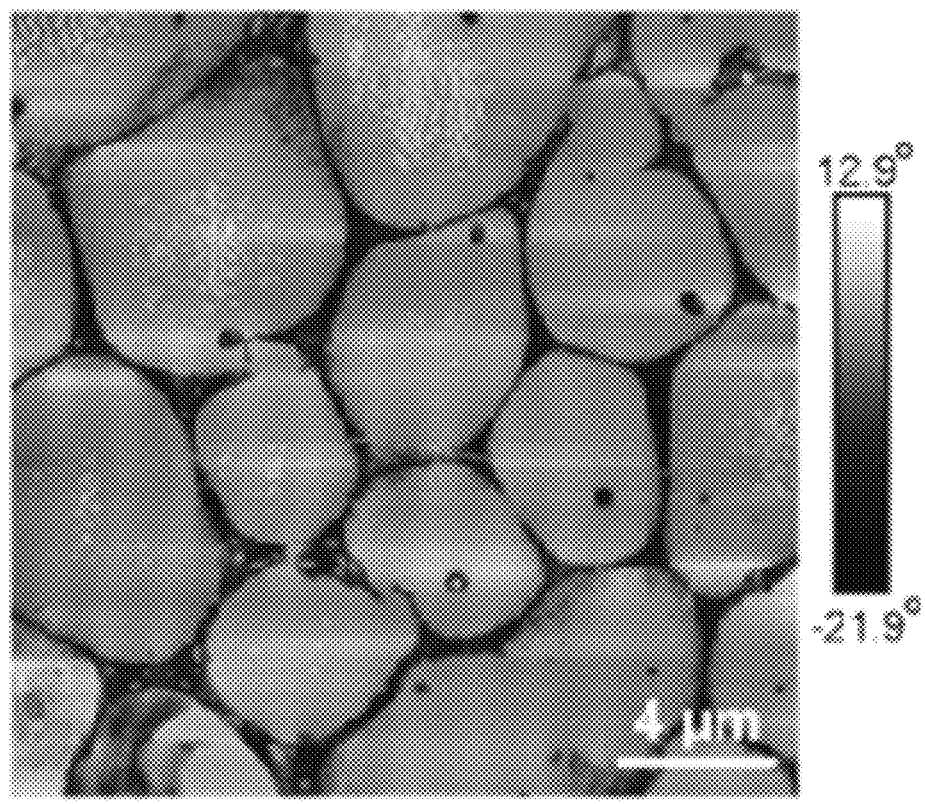
FIG. 5A is a schematic diagram illustrating an atomic force microscopy (AFM) phase analysis of hydrogel according to some embodiments of the present disclosure.
Figure 5B:
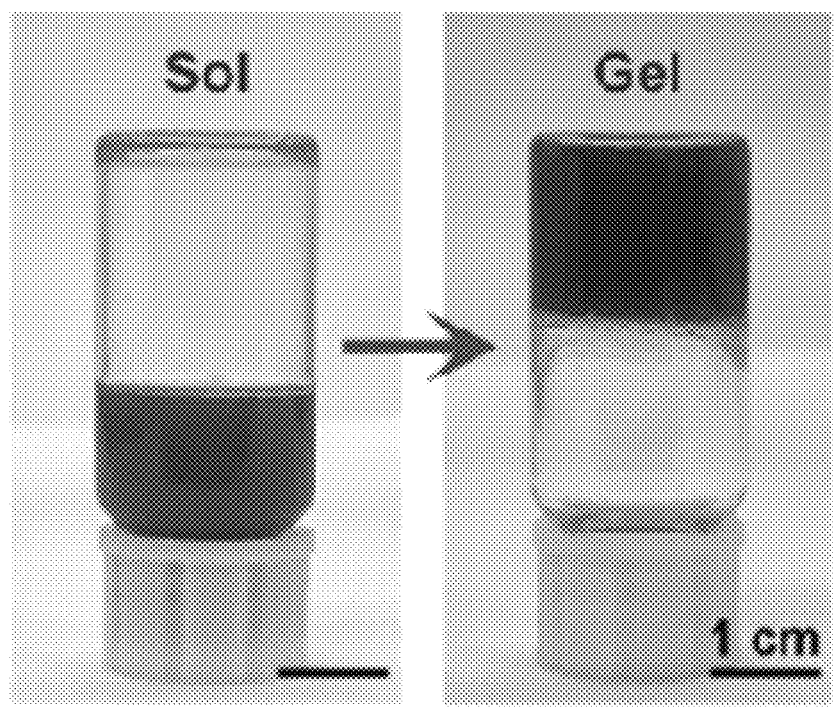
FIG. 5B is a schematic diagram illustrating an experimental transfer tube for hydrogel according to some embodiments of the present disclosure.
Figure 5C:
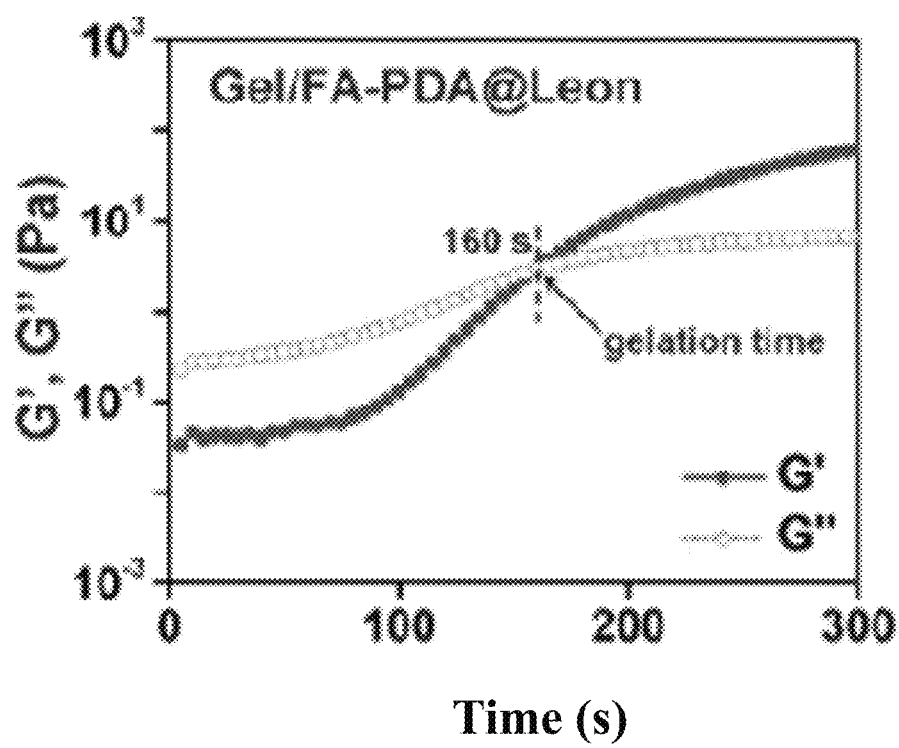
FIG. 5C is a schematic diagram illustrating a rheological analysis of hydrogel according to some embodiments of the present disclosure.
Figure 5D:
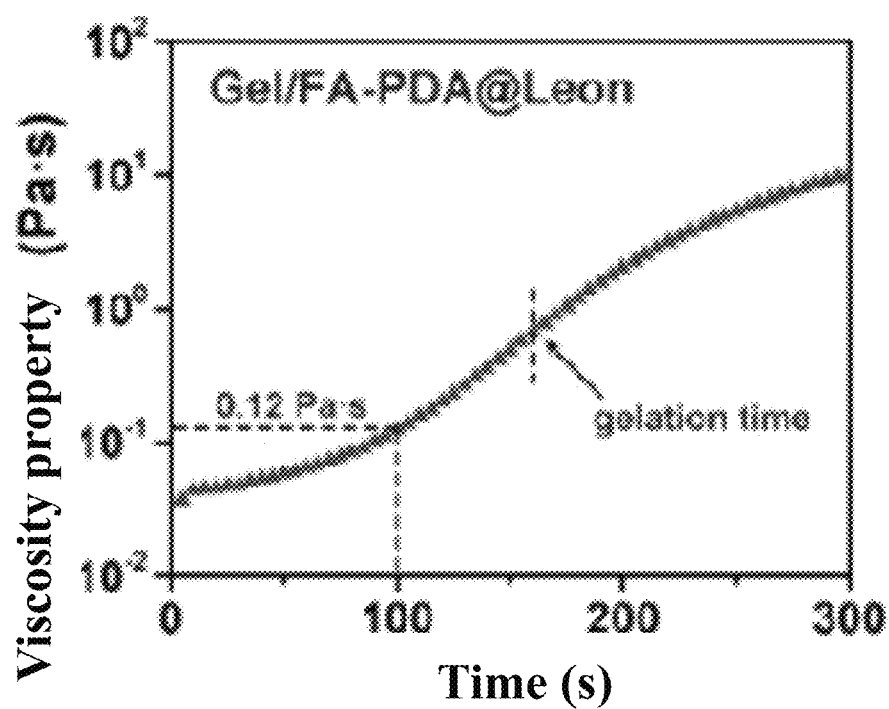
FIG. 5D is a schematic diagram illustrating an analysis of a gelation process of a hydrogel precursor according to some embodiments of the present disclosure.
Figure 5E:
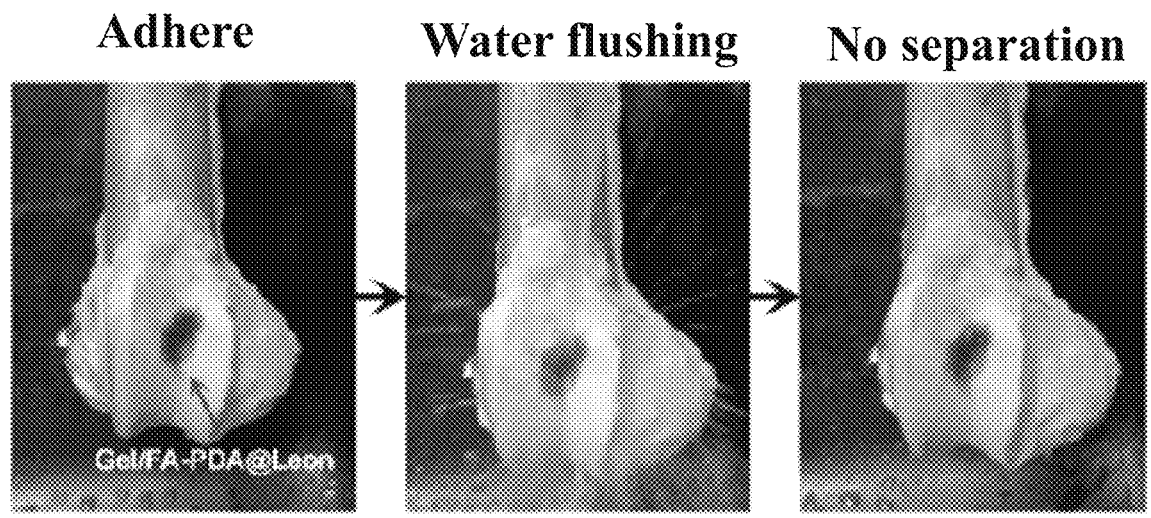
FIG. 5E is a schematic diagram illustrating an analysis of adhesion of an in situ formed gel/FA-PDA@Leon hydrogel to biological tissues according to some embodiments of the present disclosure.
Figure 5F:
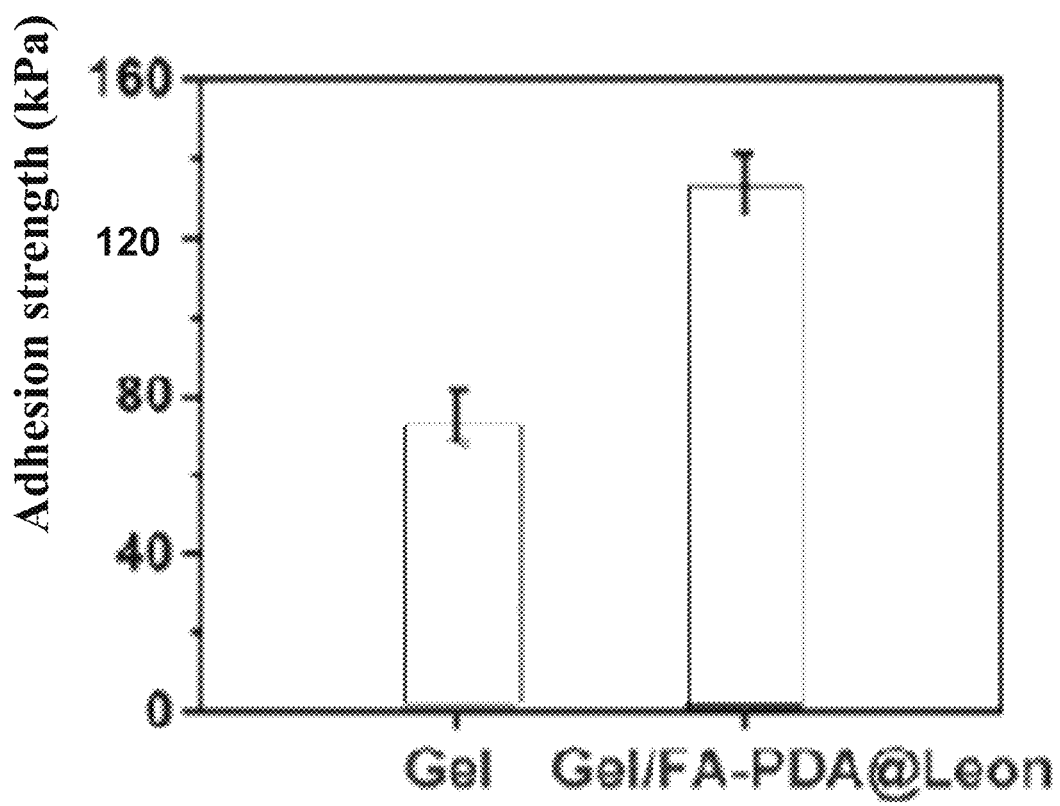
FIG. 5F is is a schematic diagram illustrating a quantitative image of an adhesion strength test of in situ-formed gel/FA-PDA@Leon hydrogel to biological tissues according to some embodiments of the present disclosure.
Figure 5G:
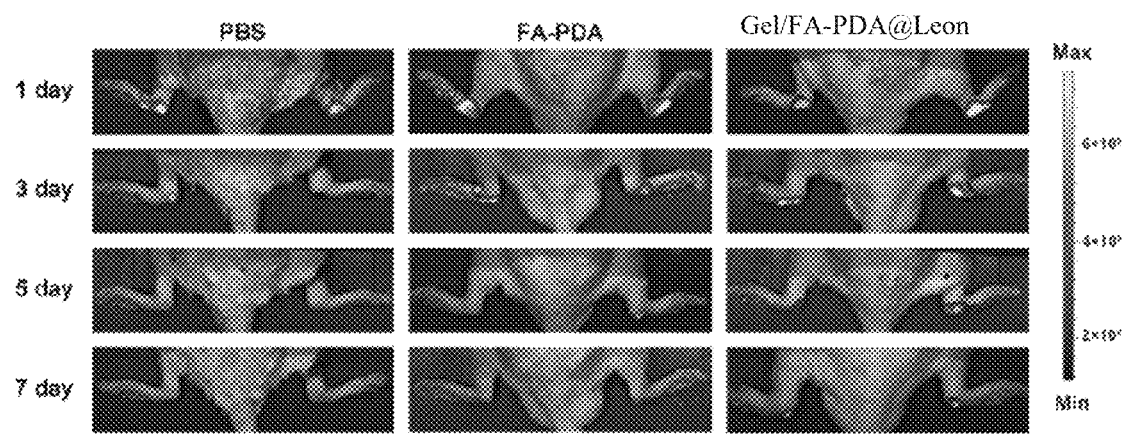
FIG. 5G is a schematic diagram illustrating distribution and retention of rhodamine-labeled FA-PDA@Leon nanodrugs tracked by a fluorescent imaging system according to some embodiments of the present disclosure.

FIG. 5A-FIG. 5G are schematic diagram illustrating evaluating anti-inflammatory activity of hydrogel and mimicking the inflammatory environment in RA. FIG. 5A is a schematic diagram illustrating an atomic force microscopy (AFM) phase analysis of hydrogel according to some embodiments of the present disclosure. FIG. 5B is a schematic diagram illustrating an experimental transfer tube for hydrogel according to some embodiments of the present disclosure. FIG. 5C is a schematic diagram illustrating a rheological analysis of hydrogel according to some embodiments of the present disclosure. FIG. 5D is a schematic diagram illustrating an analysis of a gelation process of a hydrogel precursor according to some embodiments of the present disclosure. FIG. 5E is a schematic diagram illustrating an analysis of adhesion of an in situ formed gel/FA-PDA@Leon hydrogel to biological tissues according to some embodiments of the present disclosure. FIG. 5F is a schematic diagram illustrating a quantitative image of an adhesion strength test of in situ-formed gel/FA-PDA@Leon hydrogel to biological tissues according to some embodiments of the present disclosure. FIG. 5G is a schematic diagram illustrating distribution and retention of rhodamine-labeled FA-PDA@Leon nanodrugs tracked by a fluorescent imaging system according to some embodiments of the present disclosure.

As shown in FIG. 5A, the atomic force microscopy (AFM) phase image analysis revealed that the gelatin-PEGDA image exhibited obvious phase separation features compared with the pure gelatin image, which did not differ much, with the presence of both pore-like bright areas (PEGDA-rich structural domains) and lattice-like dark areas (gelatin-rich structural domains), indicating that the gelatin chains were separated and aggregated to form a network with the PEGDA chains. This phenomenon can be explained by the fact that PEGDA can change the hydration state of the gelatin chains by excluding the solvent around the gelatin chains, which in turn drives associations between the gelatin chains.

Due to the enhanced intermolecular interactions of PEGDA-driven gelatin chains, the gel/FA-PDA@Leon hydrogels were injectable at physiological temperatures (37° C.), a key property for intra-articular delivery of nanomedicines. In the tube transfer experiments in FIG. 5B, a sol-gel (Sol)-gel transition occurs upon mixing of the FA-PDA@Leon, the gelatin, the PEGDA, and the NaOH, resulting in the formation of the gel/FA-PDA@Leon hydrogel.

As shown in FIG. 5C, rheological analysis showed that the storage modulus (G') and loss modulus (G") of the gel/FA-PDA@Leon hydrogel intersected at 160 s, further revealing the gelation time. As shown in FIG. 5D, the precursor of the hydrogel exhibited low viscosity (0.12 Pa-s at 100 s) in the early stage of the gelation process.

As shown in FIG. 5E, the in situ formed gel/FA-PDA@Leon hydrogel can tightly adhere to a surface of cartilage tissues even after being washed by water, indicating that the in situ formed gel/FA-PDA@Leon hydrogel has strong adhesive properties to biological tissues, allowing the encapsulated nanomedicine to be immobilized at the local lesion site and potentially prolonging its retention time in the joint cavity. The ability of the hydrogel to form and tightly adhere to the joint tissue within the joint cavity extends the duration of the nanomedicine treatment. The adhesion strength of the in situ formed gel/FA-PDA@Leon hydrogel to the biological tissues was quantified by the lap-shear test. Biological tissues are represented by pig skin.

The adhesion strength of the gel hydrogel is as high as 69 kPa as shown in FIG. 5F. This is due to the low viscosity of the hydrogel precursor that allows it to penetrate into tiny interstitial spaces, achieving full contact with the irregular surface of porcine skin after in situ gelation. In addition, the incorporation of FA-PDA@Leon nanodrugs enhanced the adhesion strength (124±16 kPa) of the gel/FA-PDA@Leon hydrogels, attributed to the highly active catechol moieties in the gel/FA-PDA@Leon hydrogels that facilitate interfacial bonding with biological tissues. After intra-articular injection, a fluorescent imaging system was used to track the distribution and retention of rhodamine-labeled FA-PDA@Leon nanodrugs with and without gel hydrogel encapsulation.

As shown in FIG. 5G, the gel/FA-PDA@Leon hydrogel stably resided in the rat ankle joint after injection. In contrast, a portion of the FA-PDA@Leon nanomedicine and phosphate buffer PBS diffused into the forefoot. The gel/FA-PDA@Leon hydrogel was maintained in the ankle joint cavity for up to 7 days, which was superior to FA-PDA@Leon and PBS. In vivo imaging results showed that hydrogel encapsulation improved the stability and retention time of FA-PDA@Leon nanomedicine in the joint cavity.

Embodiment 6 In Vivo Treatment of RA with Gel/FA-PDA@Leon Hydrogel

In some embodiments, an in vivo therapeutic effect of the gel/FA-PDA@Leon hydrogel on the RA is evaluated using a CIA rat model. The gel/FA-PDA@Leon hydrogel, gel/FA-PDA hydrogel, FA-PDA@Leon nanomedicine, Leon solution, and PBS solution (RA) are injected into the ankle joints of RA rats 21 and 28 days after the initial immunization, respectively, and PBS is injected into the ankle joints of normal rats as a control.

FIG. 6A-FIG. 6J schematic diagram illustrating evaluating an in vivo therapeutic effect of hydrogels.

Figure 6A:
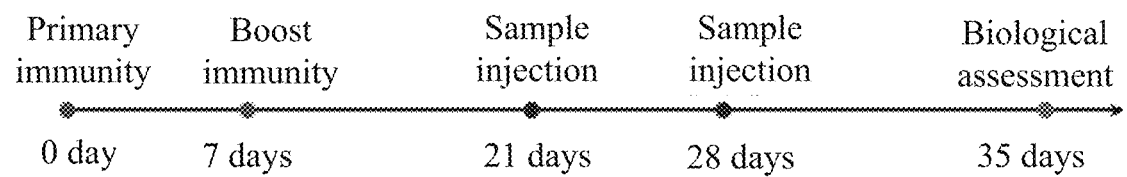
FIG. 6A is a schematic diagram illustrating a biological evaluation of rats ligated after 14 days of in vivo treatment with hydrogel according to some embodiments of the present disclosure.
Figure 6B:
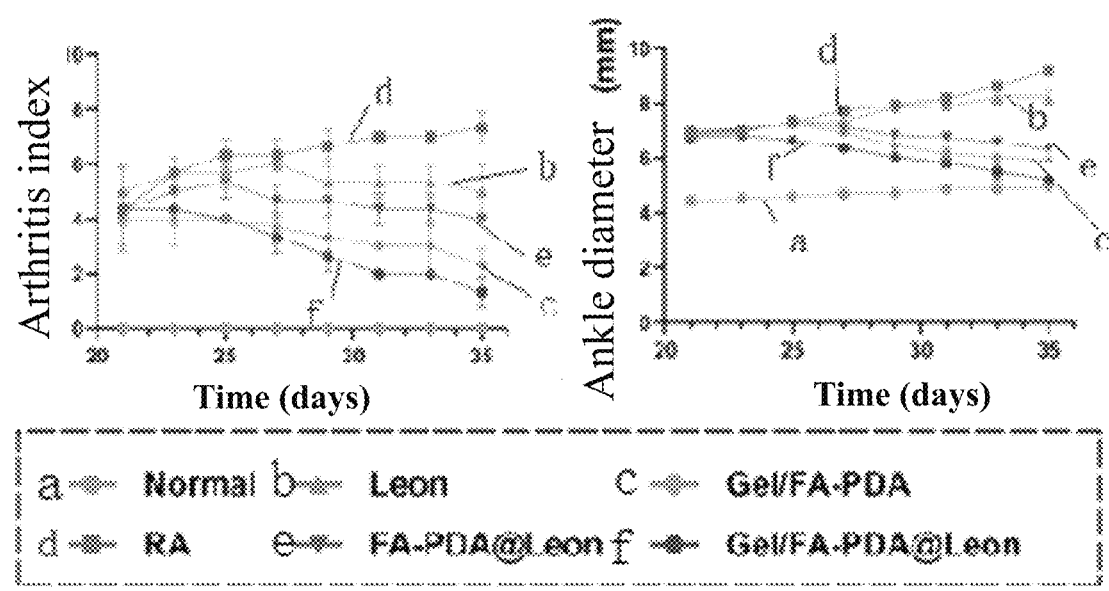
FIG. 6B is a schematic diagram illustrating arthritis indices and ankle diameters according to some embodiments of the present disclosure.
Figure 6C:
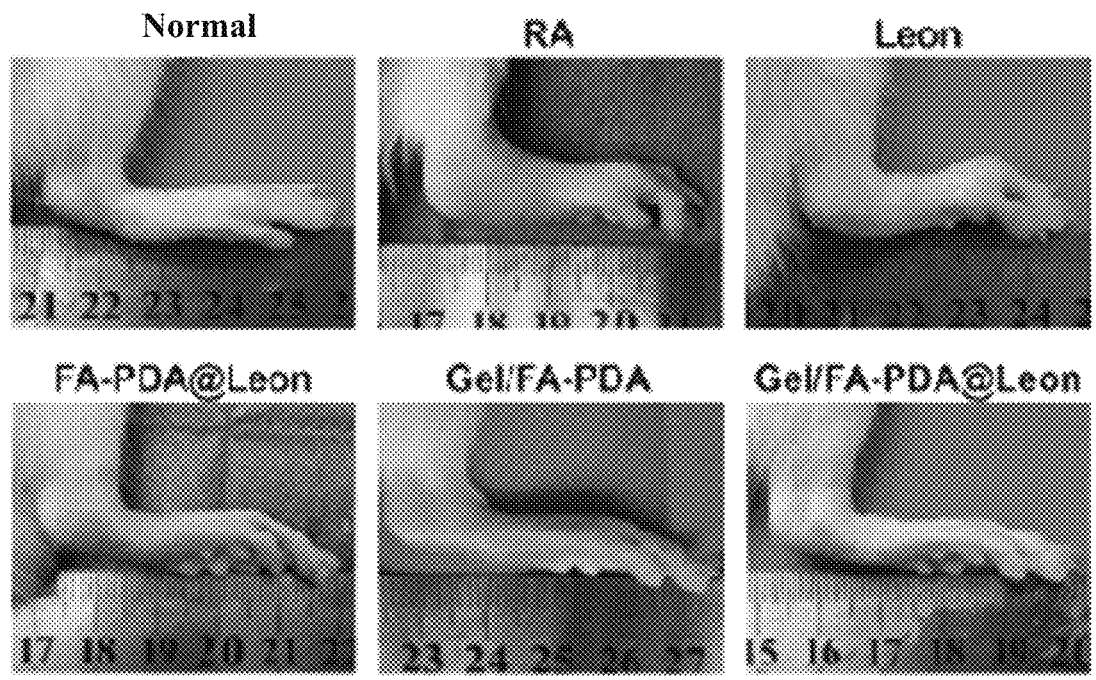
FIG. 6C is a schematic diagram illustrating hind paws after 14 days of in vivo treatment with hydrogel according to some embodiments of the present disclosure.
Figure 6D:
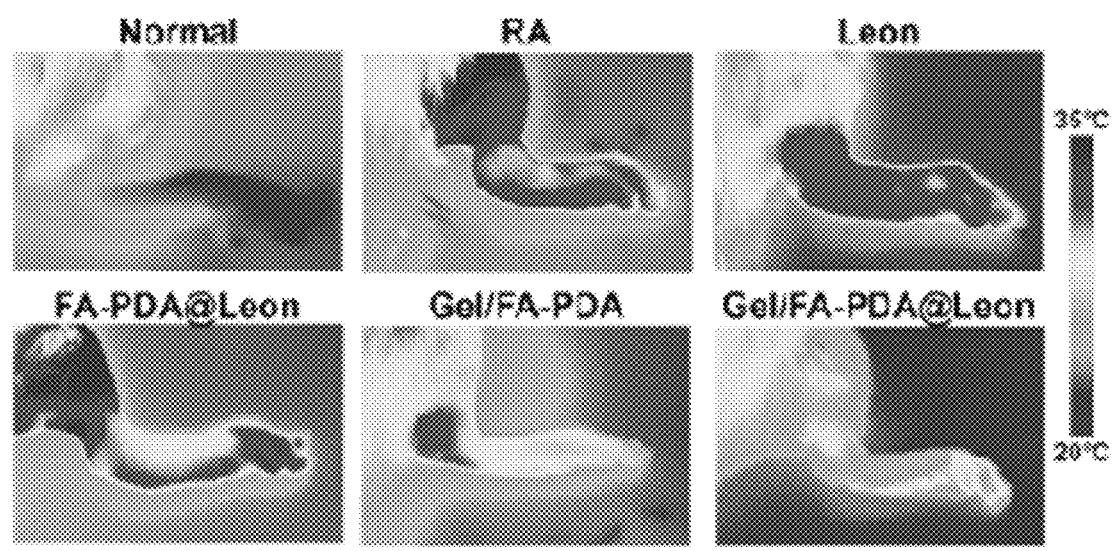
FIGS. 6D-6E are schematic diagrams illustrating localized fever in RA rats detected by a near-infrared imaging system according to some embodiments of the present disclosure.
Figure 6E:
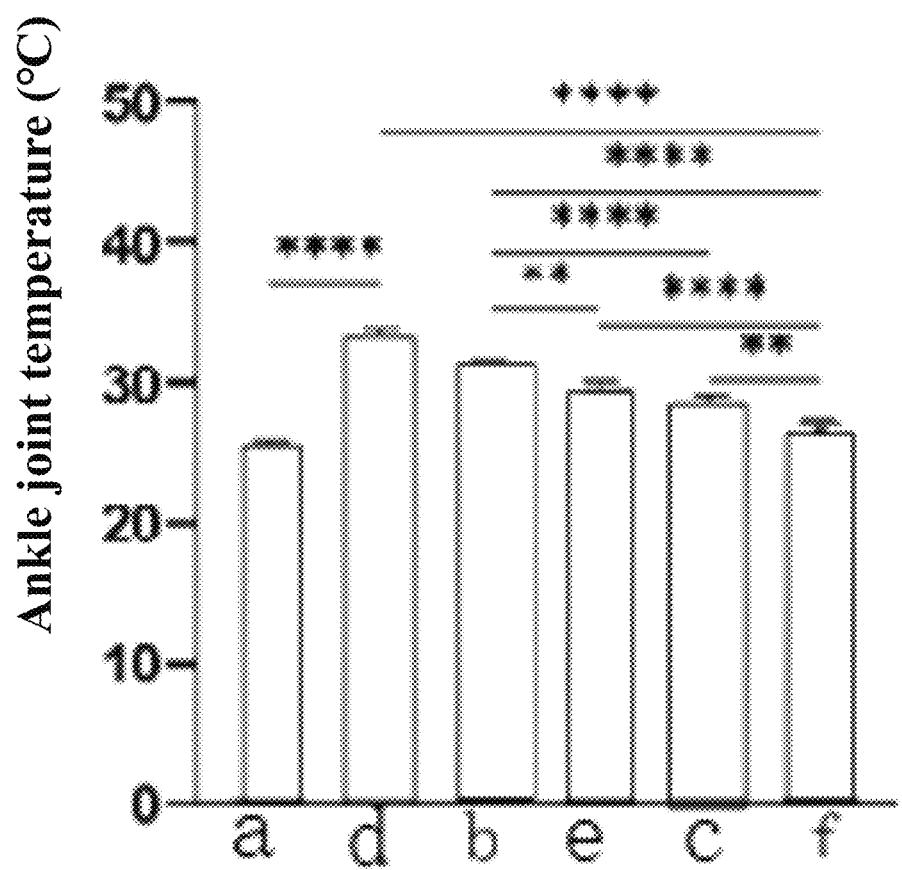
Figure 6F:
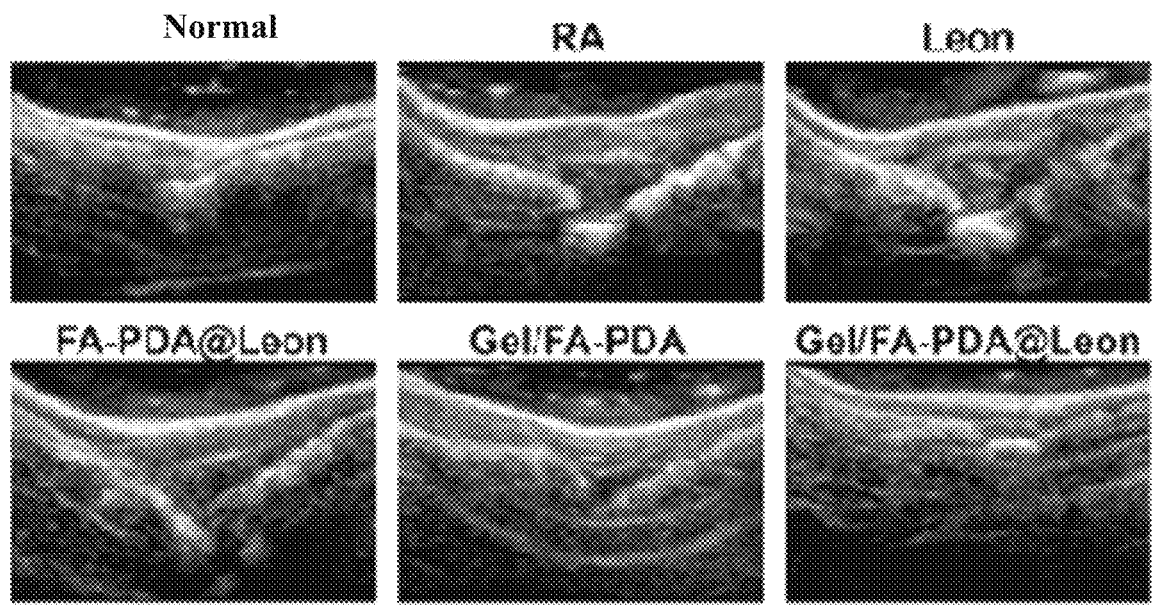
FIG. 6F are schematic diagrams illustrating progression of synovial inflammation as observed by an ultrasound imaging system according to some embodiments of the present disclosure.
Figure 6G:
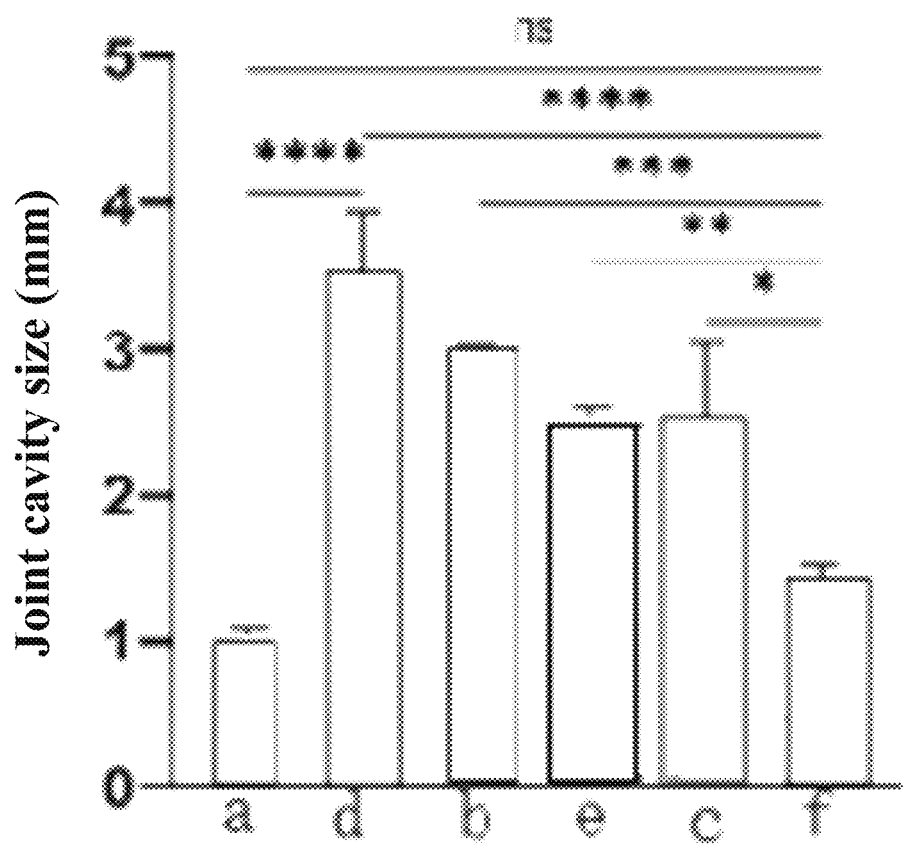
FIG. 6G is a schematic diagram illustrating a quantitative analysis of joint cavity dimension of Gel/FA-PDA@Leon hydrogel group according to some embodiments of the present disclosure.
Figure 6H:
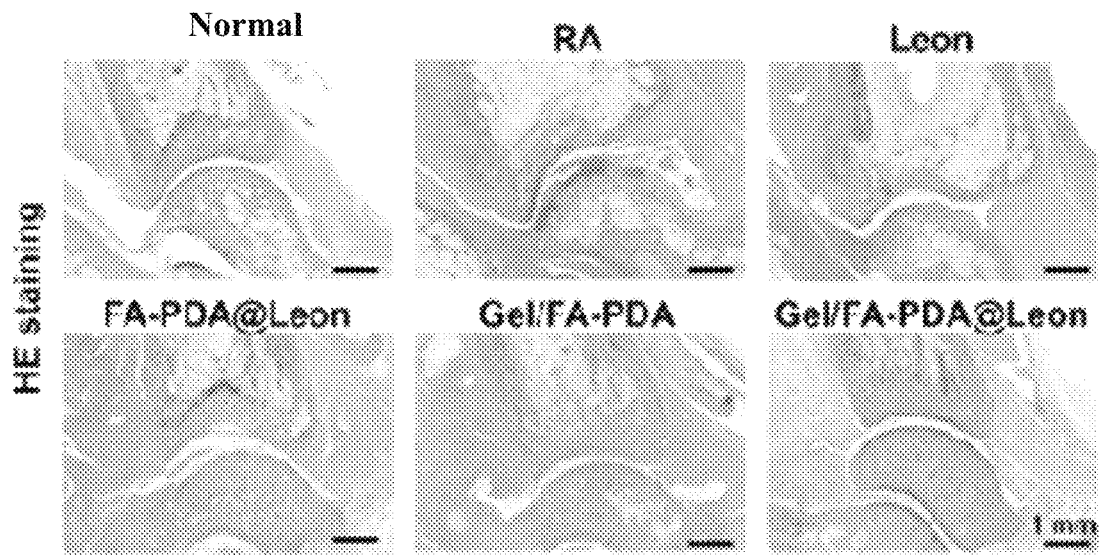
FIG. 6H are schematic diagrams illustrating an inhibitory effect of synovial inflammation at a histological level analyzed by hematoxylin-eosin (HE) staining according to some embodiments of the present disclosure.
Figure 6I:
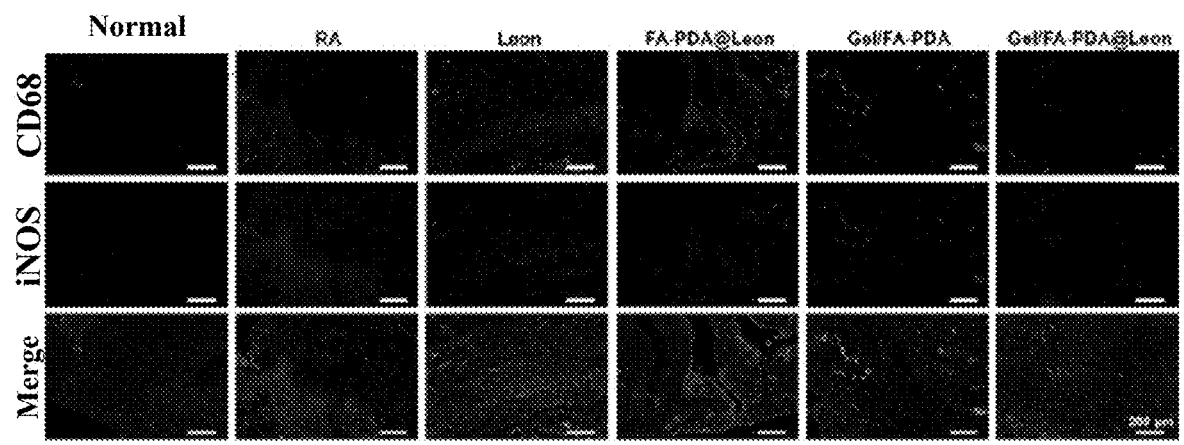
FIG. 6I is a schematic diagram illustrating a location of activated macrophages in synovial tissue as determined by immunofluorescent double staining for CD68 and iNOS according to some embodiments of the present disclosure.
Figure 6J:
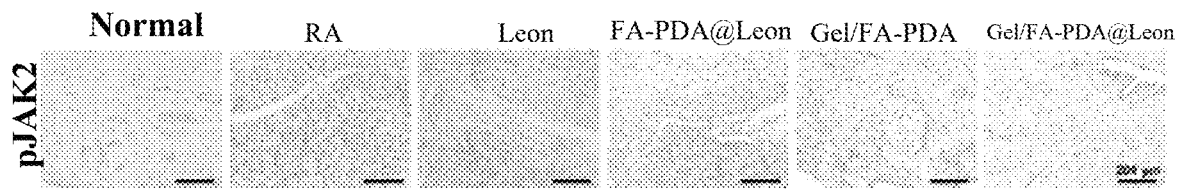
FIG. 6J is a schematic diagram illustrating an immunohistochemical staining graph according to some embodiments of the present disclosure.

FIG. 6A is a schematic diagram illustrating a biological evaluation of rats ligated after 14 days of in vivo treatment with hydrogel according to some embodiments of the present disclosure. FIG. 6B is a schematic diagram illustrating arthritis indices and ankle diameters according to some embodiments of the present disclosure. FIG. 6C is a schematic diagram illustrating hind paws after 14 days of in vivo treatment with hydrogel according to some embodiments of the present disclosure. FIG. 6D-6E are schematic diagrams illustrating localized fever in RA rats detected by a near-infrared imaging system according to some embodiments of the present disclosure. FIG. 6F are schematic diagrams illustrating progression of synovial inflammation as observed by an ultrasound imaging system according to some embodiments of the present disclosure. FIG. 6G is a schematic diagram illustrating a quantitative analysis of joint cavity dimension of Gel/FA-PDA@Leon hydrogel group according to some embodiments of the present disclosure. FIG. 6H are schematic diagrams illustrating an inhibitory effect of synovial inflammation at a histological level analyzed by hematoxylin-eosin (HE) staining according to some embodiments of the present disclosure. FIG. 6I is a schematic diagram illustrating a location of activated macrophages in synovial tissue as determined by immunofluorescent double staining for CD68 and iNOS according to some embodiments of the present disclosure. FIG. 6J is a schematic diagram illustrating an immunohistochemical staining graph according to some embodiments of the present disclosure;

As shown in FIG. 6A, after 14 days of treatment, the rats are ligated for biological evaluation.

Joint swelling and localized fever caused by synovial inflammation are pathological features of RA. As shown in FIG. 6B, to reflect a severity of swelling of the hind paw during the treatment period, clinical scores, including arthritis indices and ankle diameters, were recorded every 2 days. A decrease in clinical scores indicated that all treatment groups reduced hindpaw swelling in RA rats. In particular, the clinical scores were much lower in the gel/FA-PDA@Leon hydrogel group compared to the other treatment groups, suggesting a higher therapeutic efficacy in the gel/FA-PDA@Leon hydrogel group.

Photographs of the hind paw after 14 days of treatment as shown in FIG. 6C further confirms that the gel/FA-PDA@Leon hydrogel alleviated severe paw swelling in RA rats. Localized fever was detected in the RA rats using a near-infrared imaging system as shown in FIG. 6D-6E. The knee joints and hind paws of rats in the RA group exhibited a relatively high temperature of 33° C. due to severe synovial inflammation, which was reduced to 27° C. after treatment with the anti-inflammatory gel/FA-PDA@Leon hydrogel.

The progression of synovial inflammation was observed using an ultrasound imaging system as shown in FIG. 6F. Unexamined synovial inflammation in RA rats resulted in an enlarged joint cavity. The gel/FA-PDA@Leon hydrogel group restored the joint cavity size to a normal level due to its anti-inflammatory effect. As shown in FIG. 6G, the quantitative analysis shows that the joint cavity size of the gel/FA-PDA@Leon hydrogel group was significantly smaller than that of the other treatment groups, indicating that the gel/FA-PDA@Leon hydrogel effectively inhibited synovial proliferation.

The inhibition of synovial inflammation at the histological level was further analyzed using hematoxylin-eosin (HE) staining as shown in FIG. 6H. Minimal synovial hyperplasia and inflammatory cell infiltration were seen in the gel/FA-PDA@Leon hydrogel group sections compared to the RA and other treatment groups.

The location of activated macrophages in synovial tissues was determined by immunofluorescence double staining for CD68 and iNOS as shown in FIG. 6I. The presence of a large number of the CD68+ and iNOS+ cells in the RA group of sections suggests macrophage infiltration and activation in synovial tissue. In contrast, the number of M1 macrophages in the gel/FA-PDA@Leon hydrogel group was negligible. Immunohistochemical staining, as shown in FIG. 6J, demonstrates that an expression level of pJAK2 in synovial tissues of the RA rats was significantly reduced by treatment with the gel/FA-PDA@Leon hydrogel, suggesting that the hydrogel has a strong inhibitory effect on the JAK2/STAT3 signaling pathway in vivo.

Figure 7A:
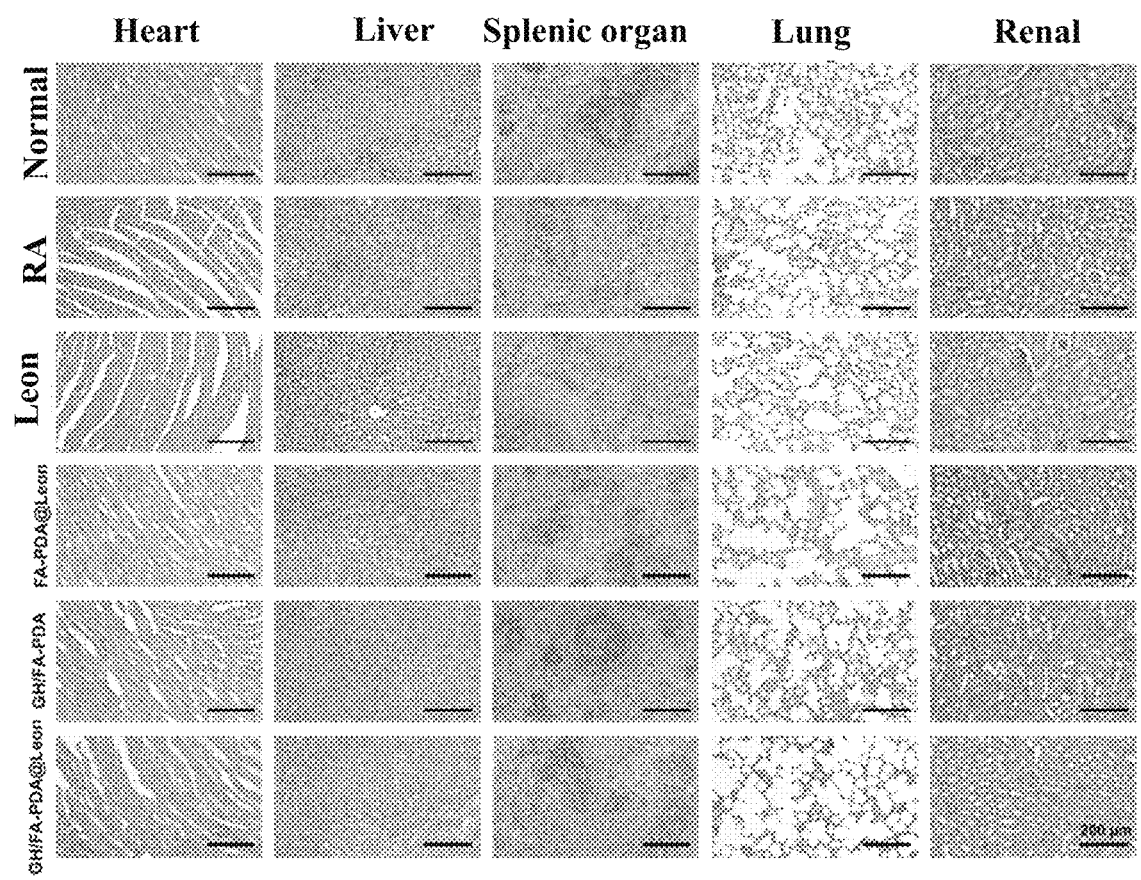
FIG. 7A is a schematic diagram illustrating evaluating toxicities of gel/FA-PDA@Leon hydrogel 14 days after implantation using HE staining and blood biochemistry analysis according to some embodiments of the present disclosure.
Figure 7B:
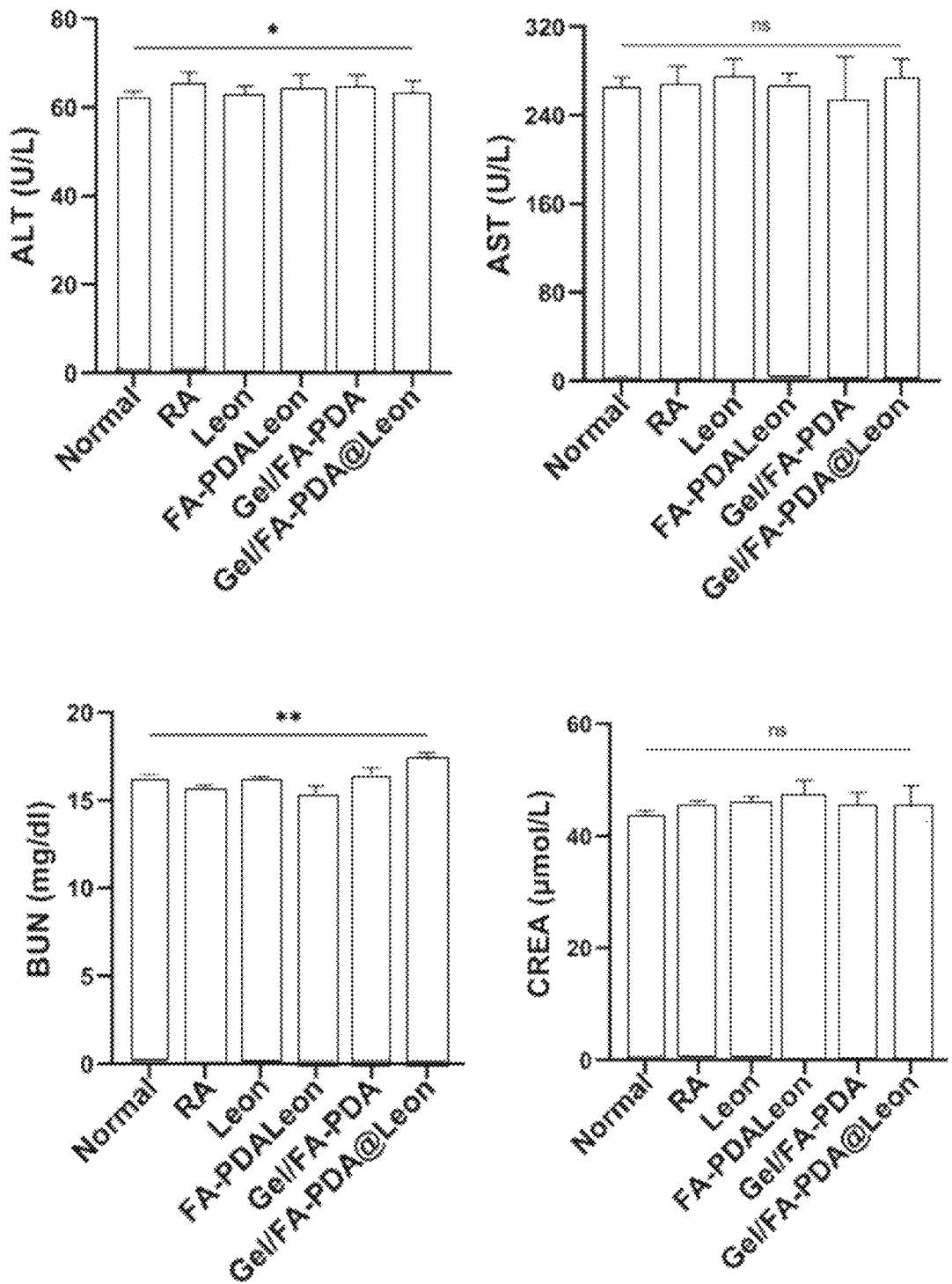
FIG. 7B are schematic diagrams illustrating blood biochemical indexes for gel/FA-PDA@Leon hydrogel groups according to some embodiments of the present disclosure.

The toxicity of the gel/FA-PDA@Leon hydrogel was evaluated 14 days after implantation using HE staining and blood biochemical analysis. FIG. 7A-FIG. 7B are schematic diagrams illustrating evaluating the in vivo biosafety of hydrogel. FIG. 7A is a schematic diagram illustrating evaluating toxicities of gel/FA-PDA@Leon hydrogel 14 days after implantation using HE staining and blood biochemistry analysis according to some embodiments of the present disclosure. FIG. 7B are schematic diagrams illustrating blood biochemical indexes for gel/FA-PDA@Leon hydrogel groups according to some embodiments of the present disclosure.

As shown in FIG. 7A, no pathological changes were observed in major organs (heart, liver, spleen, lungs, and kidneys) in the gel/FA-PDA@Leon hydrogel group compared to the normal group.

As shown in FIG. 7B, the blood biochemical indexes including alanine aminotransferase (ALT), aspartate aminotransferase (AST), blood urea nitrogen (BUN), and creatinine (CREA) in the gel/FA-PDA@Leon hydrogel group were almost comparable to those of the normal group, suggesting that an effect of the hydrogel on hepatic and renal functions was negligible. The result showed that the gel/FA-PDA@Leon hydrogel has good in vivo biosafety.

The above mentioned is only a better embodiment of the present disclosure and is not a limitation of the present disclosure in any form. Although the present disclosure has been disclosed in a better embodiment, it is not intended to limit the present disclosure. Any technician familiar with the present disclosure can make some changes or modifications as equivalent changes based on the technical contents of the present disclosure within the scope of the technical solutions of the present disclosure, but any simple modifications, equivalent changes, and modifications made to the above embodiments based on the technical substance of the present disclosure without departing from the content of the technical program of the present disclosure, all still belong to the scope of the technical program of the present disclosure.

What is claimed is:

1. A preparation method for a leonurine nanocomposite hydrogel, comprising:
    step 1: dissolving dopamine (DA) monomers and inducing oxidation and self-polymerization of the DA monomers to obtain polydopamine (PDA) nanoparticles, grafting thiol polyethylene glycol folic acid (SH-PEG-FA) on a surface of the PDA nanoparticles to obtain folic acid polydopamine (FA-PDA) nanocarriers;
    step 2: loading a leonurine (Leon) using the FA-PDA nanocarriers of the step 1 to obtain FA-PDA@Leon;
    step 3: encapsulating the FA-PDA@Leon of the step 2 into a gel matrix to obtain gel@FA-PDA@Leon hydrogel;
    wherein the gel@FA-PDA@Leon hydrogel is prepared by: dissolving gelatin and mixing the gelatin with the FA-PDA@Leon to obtain solution A, adding polyethylene glycol diacrylate (PEGDA) solution to the solution A and adding sodium hydroxide (NaOH) solution to adjust a pH value to obtain the gel@FA-PDA@Leon hydrogel; wherein a mass ratio of the gelatin to the FA-PDA@Leon is 640:1.

2. The preparation method for the leonurine nanocomposite hydrogel of claim 1, wherein a mass ratio of the FA-PDA nanocarriers to the Leon in the step 2 is 20:1.

3. The preparation method for the leonurine nanocomposite hydrogel of claim 1, wherein in the step 1, a condition for inducing the oxidation and self-polymerization of the DA monomer is stirring and reacting for 12 hours in Tris solution at 25° C. and pH 8.5.

4. The preparation method for the leonurine nanocomposite hydrogel of claim 1, wherein the pH value ranges from 6-7.

5. A leonurine nanocomposite hydrogel is obtained by using a preparation method for the leonurine nanocomposite hydrogel of claim 1.

* * * * *